(12) United States Patent
Lizardi et al.

(10) Patent No.: US 11,284,907 B2
(45) Date of Patent: *Mar. 29, 2022

(54) RETRO-CUTTING INSTRUMENT WITH ADJUSTABLE LIMIT SETTING

(71) Applicant: Medos International Sàrl, Le Locle (CH)

(72) Inventors: José E. Lizardi, Walpole, MA (US); Kevin J. Zylka, Taunton, MA (US); Scott Presbrey, Slatersville, RI (US); Michael S. Varieur, Portsmouth, RI (US); Dean C. Taylor, Durham, NC (US); Brian D. Busconi, Hopkinton, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 319 days.

This patent is subject to a terminal disclaimer.

(21) Appl. No.: 16/442,714

(22) Filed: Jun. 17, 2019

(65) Prior Publication Data

US 2019/0374235 A1 Dec. 12, 2019

Related U.S. Application Data

(63) Continuation of application No. 15/705,405, filed on Sep. 15, 2017, now Pat. No. 10,335,168, which is a
(Continued)

(51) Int. Cl.
*A61B 17/16* (2006.01)
*A61B 90/00* (2016.01)

(52) U.S. Cl.
CPC ...... *A61B 17/1617* (2013.01); *A61B 17/1622* (2013.01); *A61B 17/1675* (2013.01); *A61B 2090/031* (2016.02)

(58) Field of Classification Search
CPC .................. A61B 17/1617; A61B 17/1675
See application file for complete search history.

(56) References Cited

U.S. PATENT DOCUMENTS 5,053,044 A 10/1991 Mueller et al.
5,833,692 A 11/1998 Cesarini et al.
(Continued)

FOREIGN PATENT DOCUMENTS

JP 2003-522587 A 7/2003
JP 2011-528962 A 12/2011
(Continued)

OTHER PUBLICATIONS

U.S. Appl. No. 14/300,481, filed Jun. 10, 2014, Retro-Cutting Instrument With Adjustable Limit Setting.
(Continued)

*Primary Examiner* — Andrew Yang

(57) ABSTRACT

Cutting instruments and related methods are disclosed herein in which the diameter of the retrograde cutting blade can be adjusted to any of a plurality of diameter settings, allowing the same instrument to be used to form holes of different diameters. The limit diameter can be preset such that, during the cutting operation, the user need not be concerned with selecting the appropriate diameter, but rather can simply deploy the cutting blade until the preset limit is reached. Cutting instruments are also disclosed in which the retrograde cutting blade is distinct from the forward drilling tip and protected within a cavity formed in the body of the instrument when not in use, as are instruments in which the user is given visual and/or tactile feedback to confirm desired positioning of the cutting blade.

20 Claims, 21 Drawing Sheets

Related U.S. Application Data continuation of application No. 14/300,481, filed on Jun. 10, 2014, now Pat. No. 9,795,395.

(56) References Cited

U.S. PATENT DOCUMENTS

| | | | |
|---|---|---|---|
| 5,928,239 | A | 7/1999 | Mirza |
| 6,383,188 | B2 | 5/2002 | Kuslich et al. |
| 6,679,886 | B2 | 1/2004 | Weikel et al. |
| 6,923,813 | B2 | 8/2005 | Phillips et al. |
| 7,179,024 | B2 | 2/2007 | Greenhalgh |
| 8,246,627 | B2 | 8/2012 | Vanleeuwen et al. |
| 8,343,179 | B2 | 1/2013 | To et al. |
| 9,795,395 | B2 | 10/2017 | Lizardi et al. |
| 10,335,168 | B2 | 7/2019 | Lizardi et al. |
| 2007/0123889 | A1 | 5/2007 | Malandain et al. |
| 2009/0171359 | A1 | 7/2009 | Sterrett |
| 2010/0036381 | A1 | 2/2010 | Vanleeuwen et al. |
| 2010/0076503 | A1 | 3/2010 | Beyar et al. |
| 2011/0288553 | A1 | 11/2011 | Jansen et al. |
| 2012/0179161 | A1 | 7/2012 | Rains et al. |
| 2013/0165935 | A1 | 6/2013 | Griffiths et al. |
| 2013/0317505 | A1 | 11/2013 | To et al. |
| 2013/0325048 | A1 | 12/2013 | Weiman |
| 2014/0135779 | A1 | 5/2014 | Germain |
| 2014/0155899 | A1 | 6/2014 | Bowman et al. |
| 2014/0276844 | A1 | 9/2014 | Bourque et al. |
| 2015/0351777 | A1 | 12/2015 | Lizardi et al. |
| 2018/0008287 | A1 | 1/2018 | Lizardi et al. |

FOREIGN PATENT DOCUMENTS

| | | |
|---|---|---|
| JP | 2012-504432 A | 2/2012 |
| JP | 2012-187287 A | 10/2012 |
| WO | 2012/125546 A1 | 9/2012 |

OTHER PUBLICATIONS

U.S. Appl. No. 15/705,405, filed Sep. 15, 2017, Retro-Cutting Instrument With Adjustable Limit Setting.

[No Author] FlipCutter, A Pin that Changes Arthroscopic Tunnel Drilling Forever . . . Brochure. Arthrex, 2012 (11 pages).

[No Author] Transportal ACL Guides, Freedom in Anatomic Femoral Socket Placement. Brochure Arthrex, 2011 (2 pages).

Extended European Search Report for Application No. 15171438.3, dated Dec. 1, 2015 (9 pages).

European Examination Report for Application No. 15171438.3, dated May 30, 2017 (9 pages).

Heming, et al., "Anatomical Limitations of Transtibial Drilling in Anterior Cruciate Ligament Reconstruction", Am. J. Sports. Med., 2007; 35; 1708-1715.

Lintner, D., "Restoring the Anatomic ACL Footprint." Brochure. DePuy Mitek, Inc, 2009 (14 pages).

Japanese Office Action for Application No. 2015-116386, dated Jul. 19, 2019 (8 pages).

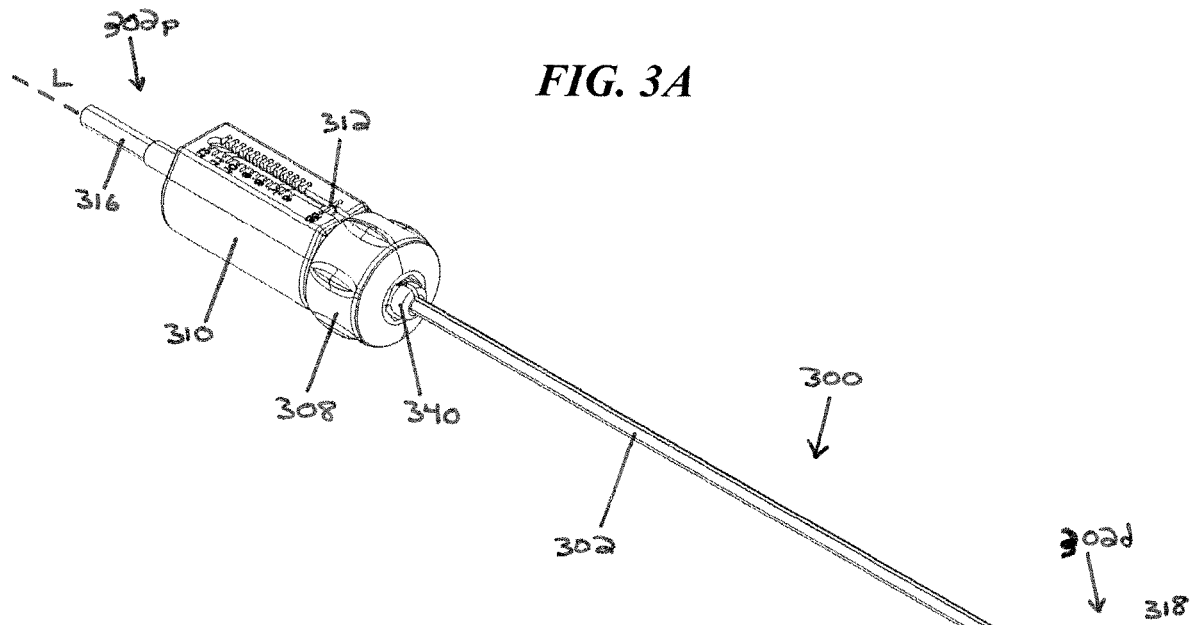
*FIG. 3A*
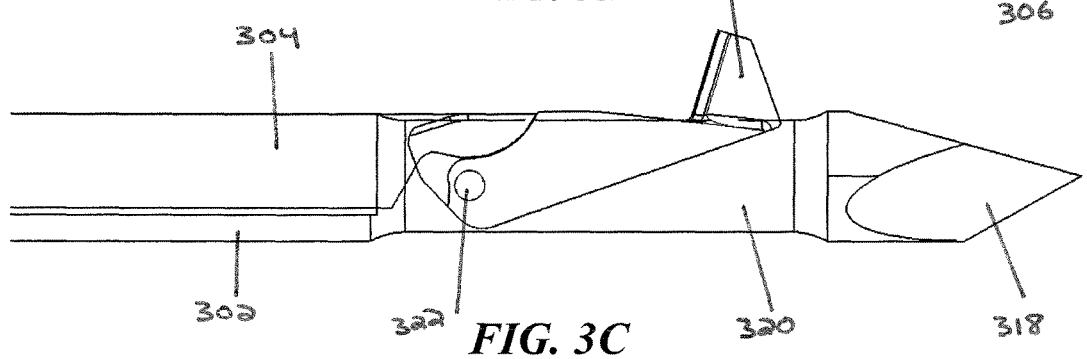
*FIG. 3B*
*FIG. 3C*
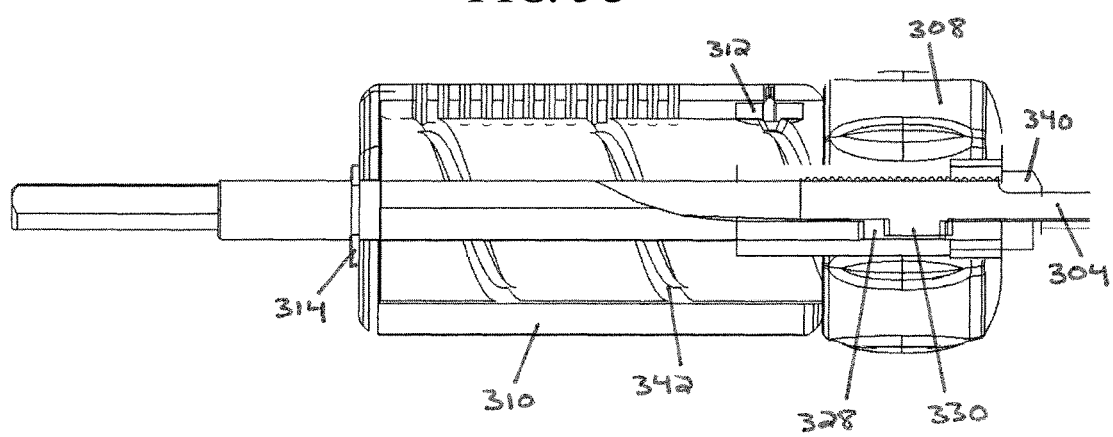

RETRO-CUTTING INSTRUMENT WITH ADJUSTABLE LIMIT SETTING

CROSS-REFERENCE TO RELATED APPLICATION

This application claims priority to and is a continuation of U.S. patent application Ser. No. 15/705,405, filed on Sep. 15, 2017, and entitled "RETRO-CUTTING INSTRUMENT WITH ADJUSTABLE LIMIT SETTING," which claims priority to and is a continuation of U.S. patent application Ser. No. 14/300,481, filed on Jun. 10, 2014, and entitled "RETRO-CUTTING INSTRUMENT WITH ADJUSTABLE LIMIT SETTING," and which issued as U.S. Pat. No. 9,795,395 on Oct. 24, 2017, the contents of each which is hereby incorporated by reference in their entireties.

FIELD

Retro-cutting instruments and related methods are disclosed herein.

BACKGROUND

During arthroscopic surgery, a small incision is made in the skin covering the arthroscopic site or joint so that surgical instruments may be placed in the joint and manipulated through arthroscopic visualization. The surgical instruments can be used to perform various tasks, such as forming a recipient site socket (e.g., a femoral or tibial bone tunnel) for receiving a soft tissue graft during reconstructive surgery.

For example, in a typical trans-tibial arthroscopic ACL procedure, a drill is used to form recipient site sockets in the tibia and the femur. The drill is first used to form a tunnel through the tibia, starting at the anterior surface of the tibia and advancing inward towards the knee joint. The resulting tibial tunnel provides access to the femur for drilling a femoral tunnel, starting within the joint space and advancing towards the exterior of the femur. Drilling of the femoral tunnel ceases when the desired depth is reached, such that the resulting femoral tunnel is a blind hole, with only a small guide wire sized hole extending all the way through to the exterior of the femur. In this trans-tibial approach, the femoral tunnel is more or less straight up and down, which is biomechanically suboptimal and reduces the rotational stability of the joint.

One way to improve joint biomechanics and rotational stability is to instead use an anteromedial portal in the femur. In an anteromedial approach, a drill is inserted through a portal formed in the front of the knee on the medial side into the femoral notch to drill a tunnel in the lateral condyle. The resulting bone tunnel is placed in a more anatomically-correct position. This approach involves several challenges, however, that arise from limitations of existing cutting instruments. For example, the surgeon must be careful when advancing the relatively large-diameter drill to avoid damaging the cartilage of the medial condyle.

An alternative method is to use an outside-in approach with a retro-cutting instrument to form a stepped opening in the femur, as shown in FIG. 1. Initially, a hole having a diameter D1 is drilled, starting at the outside of the femur and advancing inward towards the joint in the direction of the illustrated arrow A1. The drill is then partially withdrawn in the direction of the illustrated arrow A2 with a retro-cutting feature activated to widen a distal portion of the hole to a diameter D2. The retro-cutting feature is then deactivated to allow the drill to be completely withdrawn through the reduced-diameter proximal portion of the hole. There are many other procedures in which it can be desirable to form a stepped opening in a similar manner.

Existing retro-cutting instruments suffer from a number of disadvantages. For example, existing instruments can only retro-cut tunnels of a single diameter. Thus, when a need exists to drill multiple tunnels with different diameters, multiple instruments having different diameters must be used, increasing inventory and sterilization costs as well as surgical complexity.

Furthermore, in existing retro-cutting instruments, the drill tip for forward cutting and the retrograde cutting tip are one in the same. When retrograde cutting is to be performed, the forward cutting tip is simply hinged outward such that it is disposed approximately perpendicular to the main drill shaft. In this position, the open end of the main drill shaft tends to spread open and the tip can break off. Also, since the same structure is used to perform forward drilling and retrograde cutting, the shape of the structure cannot be optimized for one task or the other. This can reduce the instrument's cutting performance and/or increase the risk of the tip being damaged.

Accordingly, a need exists for improved cutting instruments and related methods.

SUMMARY

Cutting instruments and related methods are disclosed herein in which the diameter of the retrograde cutting blade can be adjusted to any of a plurality of diameter settings, allowing the same instrument to be used to form holes of different diameters. The limit diameter can be preset such that, during the cutting operation, the user need not be concerned with selecting the appropriate diameter, but rather can simply deploy the cutting blade until the preset limit is reached. Cutting instruments are also disclosed in which the retrograde cutting blade is distinct from the forward drilling tip and protected within a cavity formed in the body of the instrument when not in use, as are instruments in which the user is given visual and/or tactile feedback to confirm desired positioning of the cutting blade.

In some embodiments, a cutting instrument includes an elongate body having proximal and distal ends, the distal end defining a drilling tip, a cutting blade pivotally disposed within a cavity formed in the elongate body such that the cutting blade is positionable in a retracted position in which the cutting blade does not protrude from the elongate body and one or more deployed positions in which the cutting blade protrudes from the elongate body, an actuation shaft extending through the elongate body and having a distal end coupled to the cutting blade such that longitudinal translation of the actuation shaft relative to the elongate body is effective to move the cutting blade between the retracted position and the one or more deployed positions, an actuation knob coupled to the actuation shaft such that rotation of the actuation knob about a longitudinal axis of the elongate body is effective to longitudinally translate the actuation shaft relative to the elongate body, and an adjustment element configured to limit the degree to which the actuation shaft can be longitudinally translated relative to the elongate body based on a position of the adjustment element relative to the elongate body.

The cavity in which the cutting blade is disposed can be spaced a distance apart from the distal end of the elongate body. The actuation knob can be coupled to the actuation shaft by a threaded interface. The actuation shaft can include a first tab that extends through a first slot in the elongate body. The adjustment element can be disposed over at least a portion of the first slot to limit the degree to which the first tab can slide within the first slot. The adjustment element can include a ring having a stepped stop surface formed thereon, the stepped stop surface having a plurality of steps. Rotation of the adjustment element about the longitudinal axis of the elongate body can be effective to change which of the plurality of steps is aligned with the first slot and thereby change an effective length of the first slot. The instrument can include a fixed handle portion having a plurality of protrusions formed thereon configured to be received within a plurality of detents or openings formed in a distal-facing surface of the adjustment element. The instrument can include a bias spring configured to urge the adjustment element into engagement with the fixed handle portion. The actuation knob can include a torque limiter configured to limit the amount of torque which can be applied in rotating the actuation knob and configured to provide tactile feedback to a user when the cutting blade has reached a desired position. The distal end of the actuation shaft can be coupled to the cutting blade by a linkage mechanism. The linkage mechanism can include a link bar having a proximal end coupled to a yoke of the actuation shaft by a first cross pin and a distal end coupled to a yoke of the cutting blade by a second cross pin. Proximal translation of the actuation shaft relative to the elongate body can be effective to rotate the cutting blade about a pivot pin to retract the cutting blade into the cavity and distal translation of the actuation shaft relative to the elongate body can be effective to rotate the cutting blade about the pivot pin to deploy the cutting blade from the cavity.

In some embodiments, a cutting instrument includes an elongate body having a distal drilling tip, and a cutting blade selectively deployable from a cavity formed in the elongate body at a location proximal to the distal drilling tip, the cutting blade being deployable to any of a plurality of diameters.

In some embodiments, a method of cutting bone comprises drilling a first opening in the bone having a first diameter using a distal tip of a cutting instrument, a cutting blade of the cutting instrument being retracted into a body of the cutting instrument during said drilling; after drilling the first opening, deploying the cutting blade such that the cutting blade at least partially protrudes from the body of the cutting instrument; and, after deploying the cutting blade, cutting a second opening in the bone having a second diameter which is larger than the first diameter using the cutting blade of the cutting instrument.

The first and second openings can be contiguous with one another such that the first and second openings define a stepped bone tunnel. The first opening can be drilled in an antegrade direction and the second opening can be cut in a retrograde direction. The first opening can be drilled in an antegrade direction and the second opening can be cut in an antegrade direction. The first opening can be formed in a tibia and the second opening can be formed in a femur. The first opening can be formed in a medial portion of a femur and the second opening can be formed in a lateral portion of the femur. The method can include, after cutting the second opening, retracting the cutting blade into the body of the cutting instrument and withdrawing the cutting instrument through the first opening. The method can include setting a cutting blade deployment diameter to one of a plurality of diameter settings of the cutting instrument.

The present invention further provides devices and methods as claimed.

BRIEF DESCRIPTION OF THE DRAWINGS

The invention will be more fully understood from the following detailed description taken in conjunction with the accompanying drawings, in which:

FIG. 3A is a perspective view of another exemplary embodiment of a cutting instrument;

FIG. 3B is a sectional profile view of a distal end of the cutting instrument of FIG. 3A;

FIG. 3C is a sectional profile view of a proximal end of the cutting instrument of FIG. 3A;

DETAILED DESCRIPTION

Figure 1:
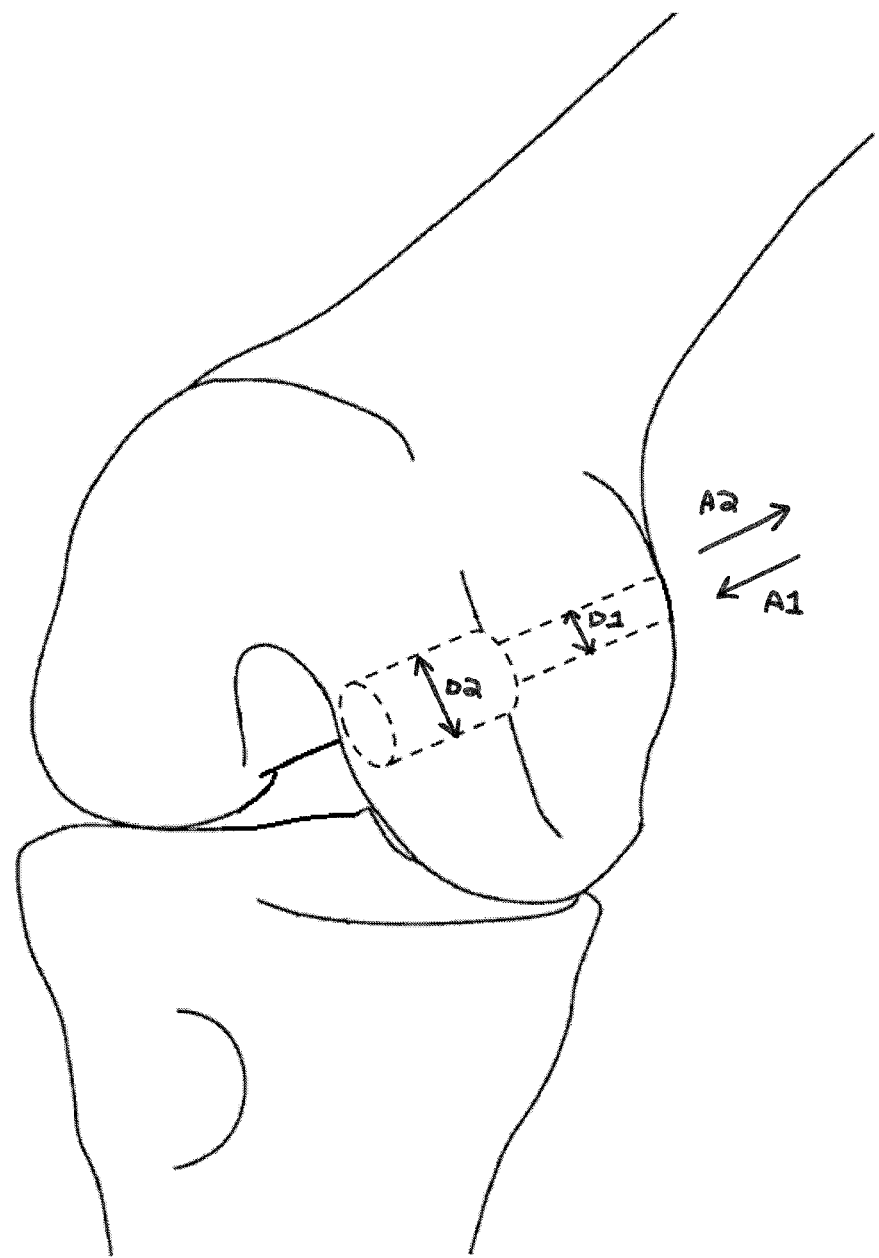
FIG. 1 is a schematic perspective view of a human knee joint with a stepped bone tunnel formed in a femur.

Cutting instruments and related methods are disclosed herein in which the diameter of the retrograde cutting blade can be adjusted to any of a plurality of diameter settings, allowing the same instrument to be used to form holes of different diameters. The limit diameter can be preset such that, during the cutting operation, the user need not be concerned with selecting the appropriate diameter, but rather can simply deploy the cutting blade until the preset limit is reached. Cutting instruments are also disclosed in which the retrograde cutting blade is distinct from the forward drilling tip and protected within a cavity formed in the body of the instrument when not in use, as are instruments in which the user is given visual and/or tactile feedback to confirm desired positioning of the cutting blade.

Certain exemplary embodiments will now be described to provide an overall understanding of the principles of the structure, function, manufacture, and use of the devices and methods disclosed herein. One or more examples of these embodiments are illustrated in the accompanying drawings. Those of skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. In the present disclosure, like-numbered components of the embodiments generally have similar features and/or purposes.

FIGS. 2A-2F illustrate an exemplary embodiment of a cutting instrument 200.

As shown, the instrument 200 generally includes an elongate body 202 that extends from a proximal end 202p to a distal end 202d along a longitudinal axis L. The instrument 200 also includes an actuation shaft 204, a cutting blade 206, an actuation knob 208 having an inner tube 210, a washer 212, and a retaining clip 214.

Figure 2A:
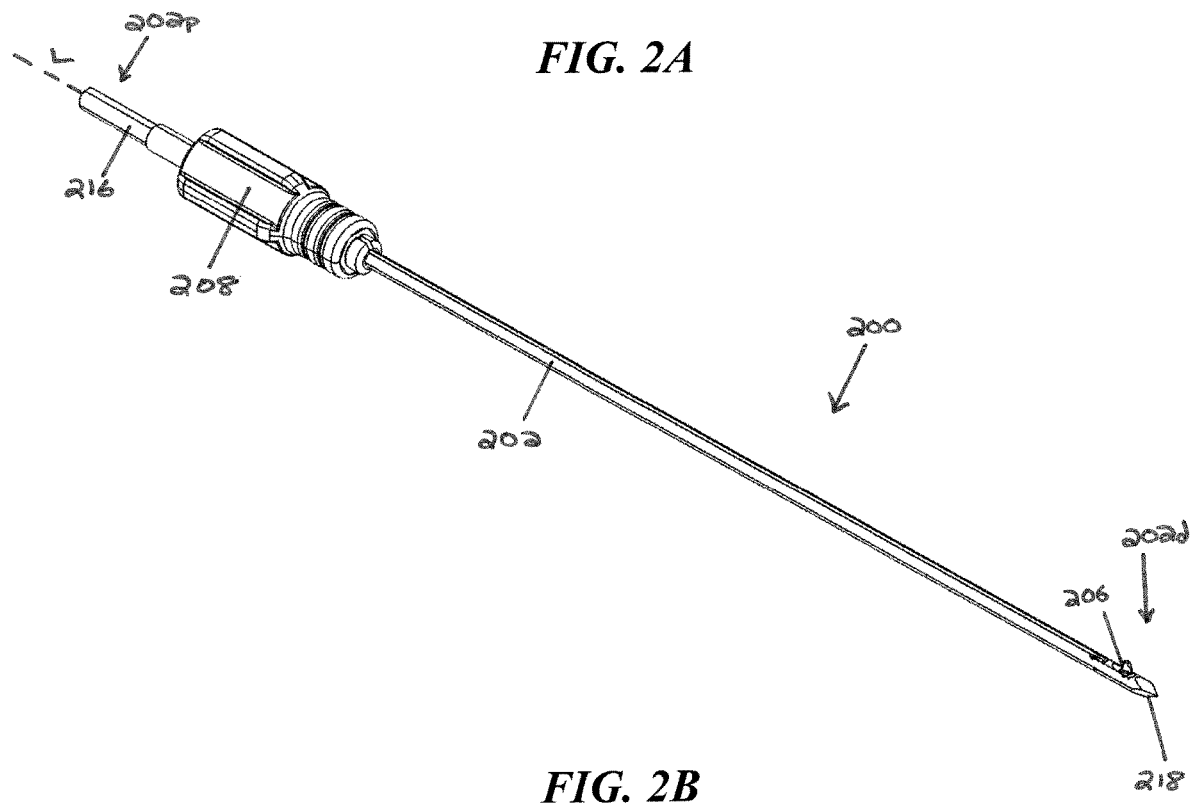
FIG. 2A is a perspective view of an exemplary embodiment of a cutting instrument.
Figure 2B:
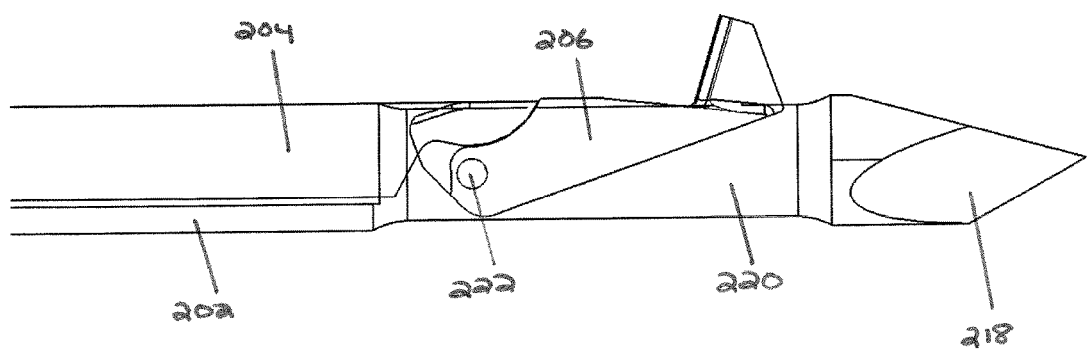
FIG. 2B is a sectional profile view of a distal end of the cutting instrument of FIG. 2A.

The proximal end of the body 202 defines a faceted mating interface or shank 216 for coupling to the chuck of a drill (e.g., an electric or pneumatic surgical drill). The distal end of the body defines a sharpened tip 218 for cutting a hole in an object in an antegrade or forward direction. The tip 218 can have any of a variety of shapes or configurations, and can be optimized for forward cutting performance. The body 202 also includes a cavity 220 in which the cutting blade is pivotally mounted via a cross pin 222. The cutting blade 206 can be selectively deployed or retracted through the opening of the cavity 220. In other words, the cutting blade 206 can be positioned in a deployed configuration, as shown in FIG. 2B, in which the blade protrudes through the opening, and a retracted configuration in which the blade does not protrude through the opening. The degree to which the blade 206 protrudes from the opening can be adjusted to adjust the diameter of the hole that is formed when the instrument 200 is used in a cutting operation. The cutting blade 206 can have any of a variety of shapes or configurations, and can be optimized for retrograde cutting and/or antegrade cutting performance.

Figure 2C:
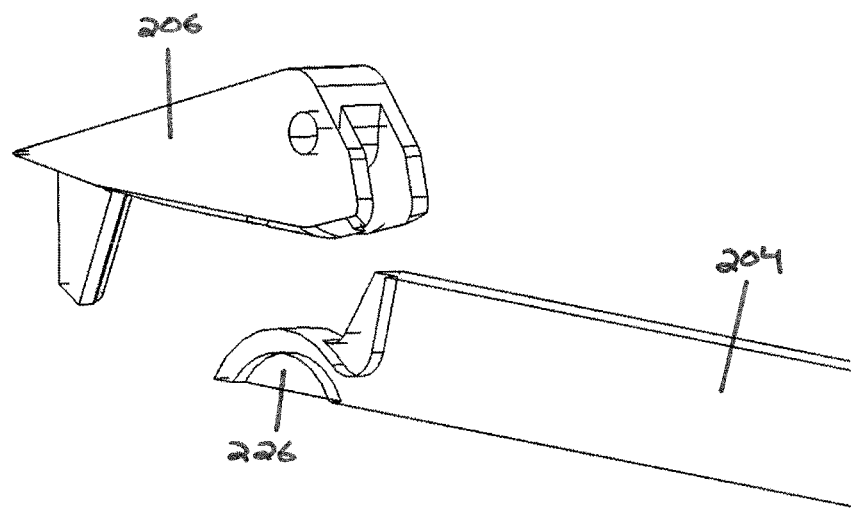
FIG. 2C is an exploded view of the actuation shaft and cutting blade of the instrument of FIG. 2A.
Figure 2D:
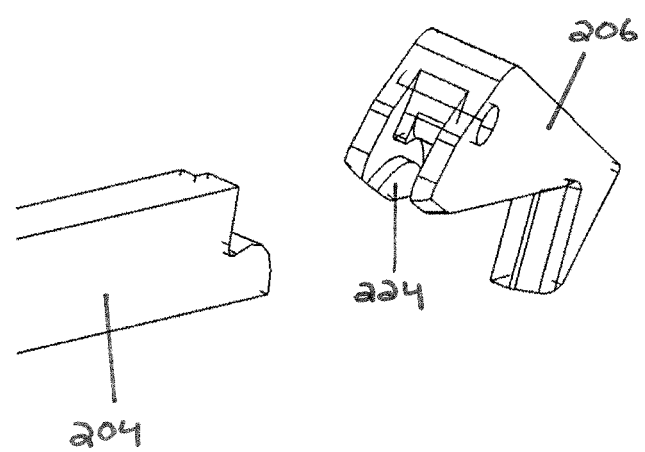
FIG. 2D is another exploded view of the actuation shaft and cutting blade of the instrument of FIG. 2A.

The actuation shaft 204 extends through an inner lumen of the body 202 and is longitudinally-translatable relative to the body. The distal end of the actuation shaft 204 can be coupled to the cutting blade 206 in any of a variety of ways. For example, as shown in FIGS. 2B-2D, the distal end of the actuation shaft 204 defines a bayonet-shaped tip that is coupled to the cutting blade 206. In particular, the proximal end of the cutting blade 206 defines a yoke in which the distal end of the actuation shaft 204 is received. A male projection 224 formed on the interior of the yoke defines a curved camming surface that engages a corresponding curved camming surface of a female receptacle 226 formed in the tip of the actuation shaft 204. In operation, proximal translation of the actuation shaft 204 relative to the body 202 causes the blade 206 to pivot about the cross pin 222 and to be deployed through the opening. The degree to which the actuation shaft 204 is translated proximally controls the degree to which the cutting blade 206 protrudes from the opening. Distal translation of the actuation shaft 204 relative to the body 202 causes the blade 206 to pivot in the opposite direction about the cross pin 222 and to be retracted into the cavity.

Figure 2E:
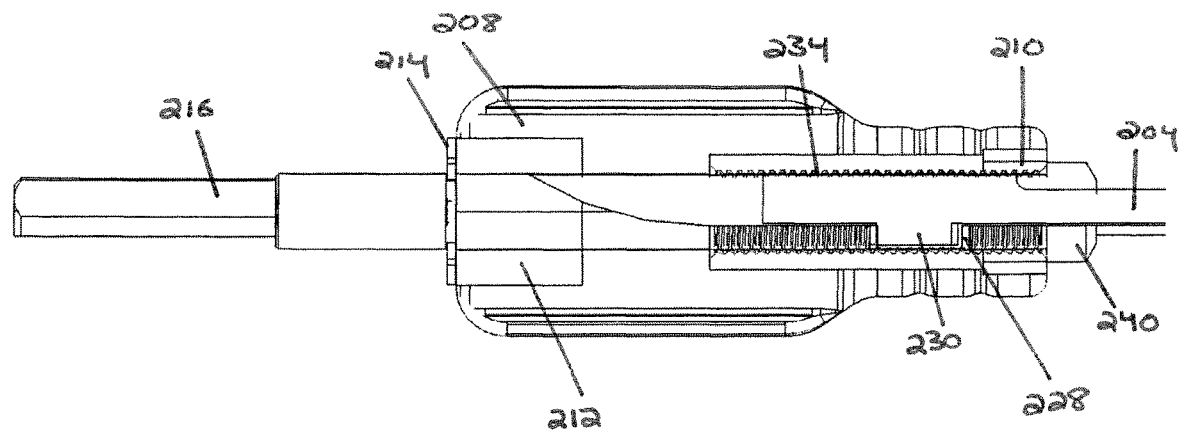
FIG. 2E is a sectional profile view of a proximal end of the cutting instrument of FIG. 2A.
Figure 2F:
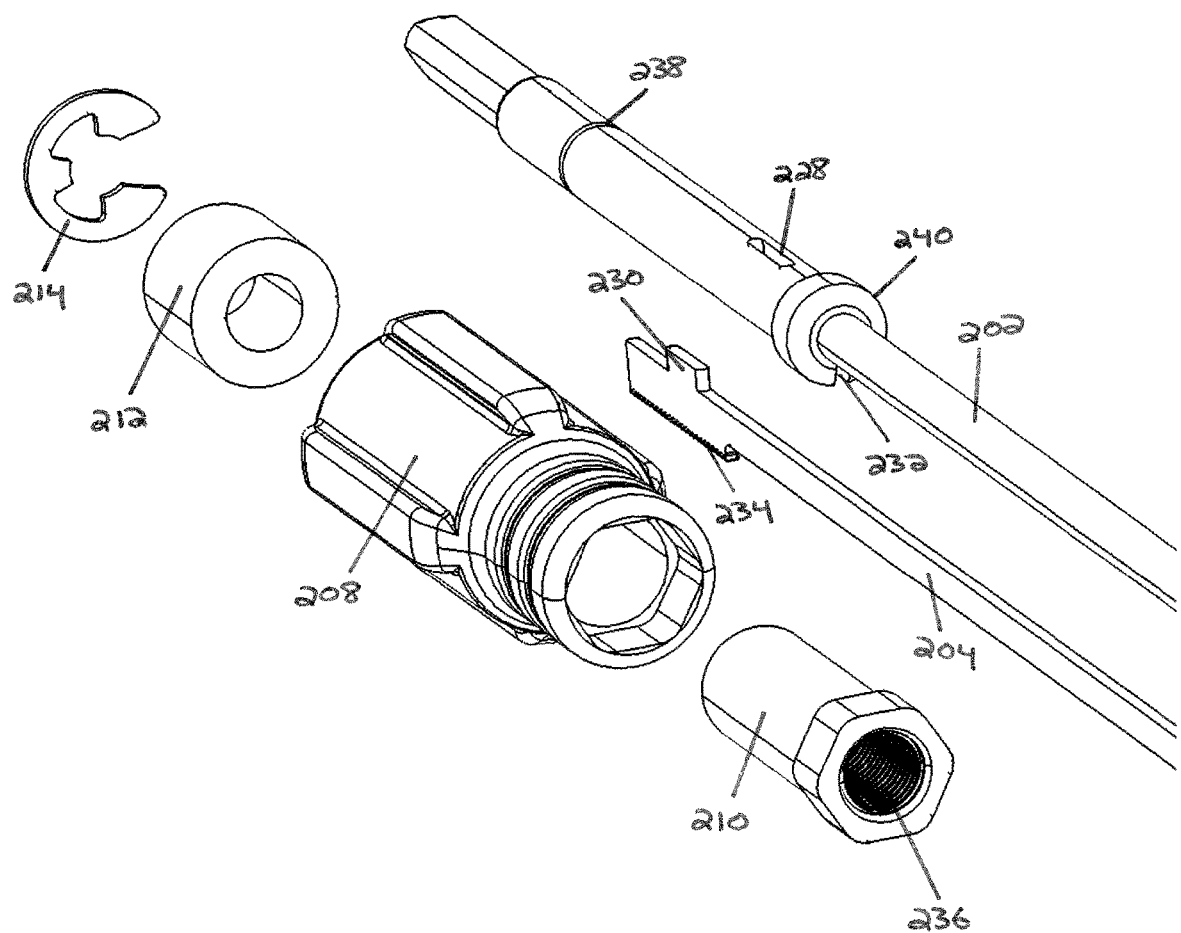
FIG. 2F is an exploded view of the proximal end of the cutting instrument of FIG. 2A.

As shown in FIGS. 2E-2F, a cylindrical proximal portion of the body defines a first longitudinal slot 228 in which a first tab portion 230 of the actuation shaft 204 is slidably positioned. The slot 228 has a length that is greater than the length of the tab 230, such that the tab can slide longitudinally within the slot between a proximal position in which the blade 206 is fully-deployed and a distal position in which the blade is fully-retracted. The length of the slot 228 thus defines the range of diameters to which the blade 206 can be deployed and therefore the range of tunnel diameters that can be formed by the blade.

The cylindrical proximal portion of the body 202 also defines a second longitudinal slot 232 in which a second tab portion 234 of the actuation shaft 204 is slidably positioned. The inner tube 210 of the actuation knob 208 is rotatably positioned over the cylindrical proximal portion of the body 202 such that a threaded interior surface 236 of the inner tube engages a threaded surface of the second tab 234 of the actuation shaft 204. The actuation knob 208 is positioned over the inner tube 210 such that the inner tube sits within a distal cylindrical recess formed in the actuation knob. A hexagonal male portion of the inner tube 210 engages a hexagonal female portion of the actuation knob 208 to fix the rotational position of the actuation knob relative to the inner tube. The washer 212 is disposed in a proximal cylindrical recess formed in the actuation knob 208 and held in place by a retaining clip 214 that snaps into a slot 238 formed in the exterior surface of the body 202. The actuation knob 208 is sandwiched between the retaining clip 214 and a shoulder 240 formed on the body 202 to maintain the actuation knob at a fixed longitudinal position relative to the body. Accordingly, rotation of the actuation knob 208 (and the inner tube 210 coupled thereto) relative to the body 202 causes the threads of the actuation shaft 204 to ride along the threads of the inner tube, thus causing the actuation shaft to translate longitudinally relative to the body. The proximal and distal limits of this longitudinal translation are defined by the size of the first slot 228 relative to the first tab 230 formed on the actuation shaft 204. The actuation knob 208 can be rotated in a first direction about the longitudinal axis L to pull the actuation shaft 204 proximally and deploy the blade 206 and/or increase the cutting diameter. The actuation knob 208 can also be rotated in a second, opposite direction about the longitudinal axis L to push the actuation shaft 204 distally and retract the blade 206 and/or decrease the cutting diameter.

While a threaded interface for advancing and retracting the actuation shaft 204 is shown, it will be appreciated that various other mechanisms can be used instead or in addition. In some embodiments, the threaded interface advantageously provides increased mechanical advantage for moving the cutting blade 206, which can prevent the cutting blade from getting stuck in the deployed or retracted positions during a cutting operation. In addition, while a rotatable actuation knob is shown and described herein, it will be appreciated that any of a variety of actuation mechanisms can be used instead or in addition, including buttons, levers, triggers, and so forth.

In an exemplary method of using the instrument 200, the instrument can be prepared for use by coupling the instrument to a drill and rotating the actuation handle 208 to position the blade 206 in the fully-retracted position. When the surgeon is ready to form a stepped opening, the surgeon actuates the drill to form the reduced diameter portion of the opening with the forward cutting tip 218. The surgeon then rotates the actuation handle 208 until further rotation is not possible, indicating that the blade 206 has been deployed. The surgeon then actuates the drill to retro-cut the enlarged diameter portion of the stepped opening. Finally, the surgeon rotates the actuation handle 208 to return the cutting blade 206 to the fully-retracted position and withdraws the instrument 200 from the patient. The instrument 200 can also be used in other exemplary methods, as described further below.

FIGS. 3A-3E illustrate another exemplary embodiment of a cutting instrument 300.

As shown, the instrument 300 generally includes an elongate body 302 that extends from a proximal end 302p to a distal end 302d along a longitudinal axis L. The instrument 300 also includes an actuation shaft 304, a cutting blade 306, an actuation knob 308, a handle 310, a slide indicator 312, and a retaining clip 314.

The proximal end of the body 302 defines a faceted mating interface or shank 316 for coupling to the chuck of a drill (e.g., an electric or pneumatic surgical drill). The distal end of the body 302 defines a sharpened tip 318 for cutting a hole in an object in an antegrade or forward direction. The tip 318 can have any of a variety of shapes or configurations, and can be optimized for forward cutting performance. The body 302 also includes a cavity 320 in which the cutting blade 306 is pivotally mounted via a cross pin 322. The cutting blade 306 can be selectively deployed or retracted through the opening of the cavity 320. In other words, the cutting blade 306 can be positioned in a deployed configuration, as shown in FIG. 3B, in which the blade protrudes through the opening, and a retracted configuration in which the blade does not protrude through the opening. The degree to which the blade 306 protrudes from the opening can be adjusted to adjust the diameter of the hole that is formed when the instrument 300 is used in a cutting operation. The cutting blade 306 can have any of a variety of shapes or configurations, and can be optimized for retrograde cutting and/or antegrade cutting performance.

The actuation shaft 304 extends through an inner lumen of the body 302 and is longitudinally-translatable relative to the body. The distal end of the actuation shaft 304 can be coupled to the cutting blade 306 in any of a variety of ways. For example, as shown in FIG. 3B, the distal end of the actuation shaft 304 defines a bayonet-shaped tip that is coupled to the cutting blade 306 (e.g., in the same manner as discussed above with respect to the instrument 200). In operation, proximal translation of the actuation shaft 304 relative to the body 302 causes the blade 306 to pivot about the cross pin 322 and to be deployed through the opening. The degree to which the actuation shaft 304 is translated proximally controls the degree to which the cutting blade 306 protrudes from the opening. Distal translation of the actuation shaft 304 relative to the body 302 causes the blade 306 to pivot in the opposite direction about the cross pin 322 and to be retracted into the cavity 320.

Figure 3D:
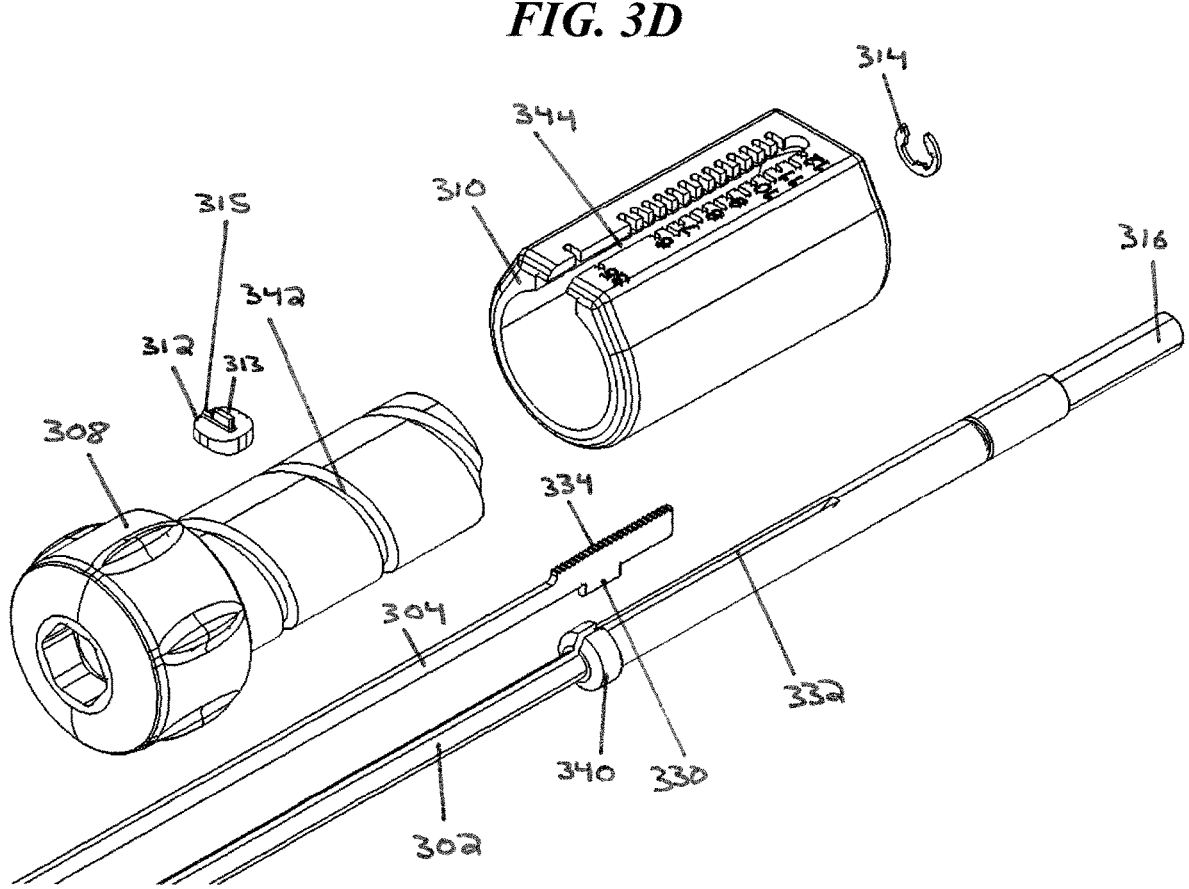
FIG. 3D is an exploded view of the proximal end of the cutting instrument of FIG. 3A.

As shown in FIGS. 3C-3D, a cylindrical proximal portion of the body 302 defines a first longitudinal slot 328 in which a first tab portion 330 of the actuation shaft 304 is slidably positioned. The slot 328 has a length that is greater than the length of the tab 330, such that the tab can slide longitudinally within the slot between a proximal position in which the blade 306 is fully-deployed and a distal position in which the blade is fully-retracted. The length of the slot 328 thus defines the range of diameters to which the blade 306 can be deployed and therefore the range of tunnel diameters that can be formed by the blade.

The cylindrical proximal portion of the body 302 also defines a second longitudinal slot 332 in which a second tab portion 334 of the actuation shaft 304 is slidably positioned. The actuation knob 308 is rotatably positioned over the cylindrical proximal portion of the body 302 such that a threaded interior surface of the actuation knob engages a threaded surface of the second tab 334 of the actuation shaft 304.

The actuation knob 308 is substantially cylindrical and includes a large pitch exterior thread 342 in which a lower portion of the slide indicator 312 is slidably disposed. The actuation knob 308 is received within the handle 310 such that the actuation knob is rotatable relative to the handle and such that an upper portion of the slide indicator 312 is slidably disposed in a slot 344 formed in the handle. The handle 310 and the actuation knob 308 are sandwiched between a proximal retaining clip 314 and a shoulder 340 formed on the body 302 to maintain the actuation knob at a fixed longitudinal position relative to the body. The handle portion 310 can optionally be rotatably fixed relative to the body 302. In operation, rotation of the actuation knob 308 relative to the body 302 and the handle portion 310 causes the threads of the actuation shaft 304 to ride along the threads of actuation knob, thus causing the actuation shaft to translate longitudinally relative to the body. The proximal and distal limits of this longitudinal translation are defined by the size of the first slot 328 relative to the first tab 330 formed on the actuation shaft 304. The actuation knob 308 can be rotated in a first direction about the longitudinal axis L to pull the actuation shaft 304 proximally and deploy the blade 306 and/or increase the cutting diameter. The actuation knob 308 can also be rotated in a second, opposite direction about the longitudinal axis L to push the actuation shaft 304 distally and retract the blade 306 and/or decrease the cutting diameter.

Figure 3E:
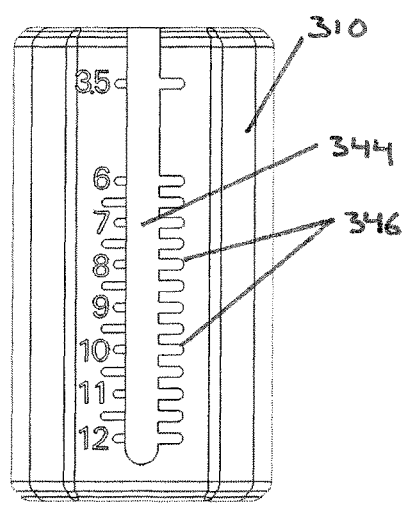
FIG. 3E is a plan view of a handle portion of the cutting instrument of FIG. 3A.

The instrument 300 also defines a number of intermediate stop points between the fully-deployed and the fully-retracted blade positions. As the actuation knob 308 rotates, the slide indicator 312 rides in the large pitch thread 342. The indicator 312 is captive in the slot 344 formed in the handle 310, such that the indicator translates longitudinally relative to the handle as the actuation knob 308 is rotated. The indicator 312 includes a main protrusion 313 that indicates the selected cutting diameter. The indicator 312 also includes a second protrusion 315 adjacent to the main protrusion that interfaces with a plurality of lateral branches 346 of the slot 344 as the actuation knob 308 is rotated. When the second protrusion 315 clicks into a lateral branch 346, the user receives tactile feedback that the next diameter setting has been reached. Markings can be printed or otherwise formed on the handle 310 to provide an indication to the user as to the extent of blade deployment. In the illustrated embodiment, as shown in FIG. 3E, numerical graduations are included to represent the available cutting diameter settings in millimeters (e.g., 3.5 mm diameter in the fully-retracted position and diameters of 6 to 12 mm in one millimeter increments for the various deployed positions). As also shown in FIG. 3E, the lateral slots 346 can define half millimeter increments between each full millimeter setting. It will be appreciated that these available diameters are merely exemplary and, as discussed below, the instrument 300 can be configured to provide any of a variety of diameters or ranges of diameters.

In an exemplary method of using the instrument 300, the instrument can be prepared for use by coupling the instrument to a drill and rotating the actuation handle 308 to position the blade 306 in the fully-retracted position. When the surgeon is ready to form a stepped opening, the surgeon actuates the drill to form the reduced diameter portion of the opening with the forward cutting tip 318. The surgeon then rotates the actuation knob 308 until the desired hole diameter is indicated by the slide indicator 312 and the handle 310. The surgeon then actuates the drill to retro-cut the enlarged diameter portion of the stepped opening. Finally, the surgeon rotates the actuation knob 308 to return the cutting blade 306 to the fully-retracted position and withdraws the instrument 300 from the patient. The instrument 300 can also be used in other exemplary methods, as described further below.

FIGS. 4A-4F illustrate another exemplary embodiment of a cutting instrument 400.

As shown, the instrument 400 generally includes an elongate body 402 that extends from a proximal end 402p to a distal end 402d along a longitudinal axis L. The instrument 400 also includes an actuation shaft 404, a cutting blade 406, an actuation knob 408, a disc handle 410, a stop ring 412, and an adjustment knob 448.

Figure 4A:
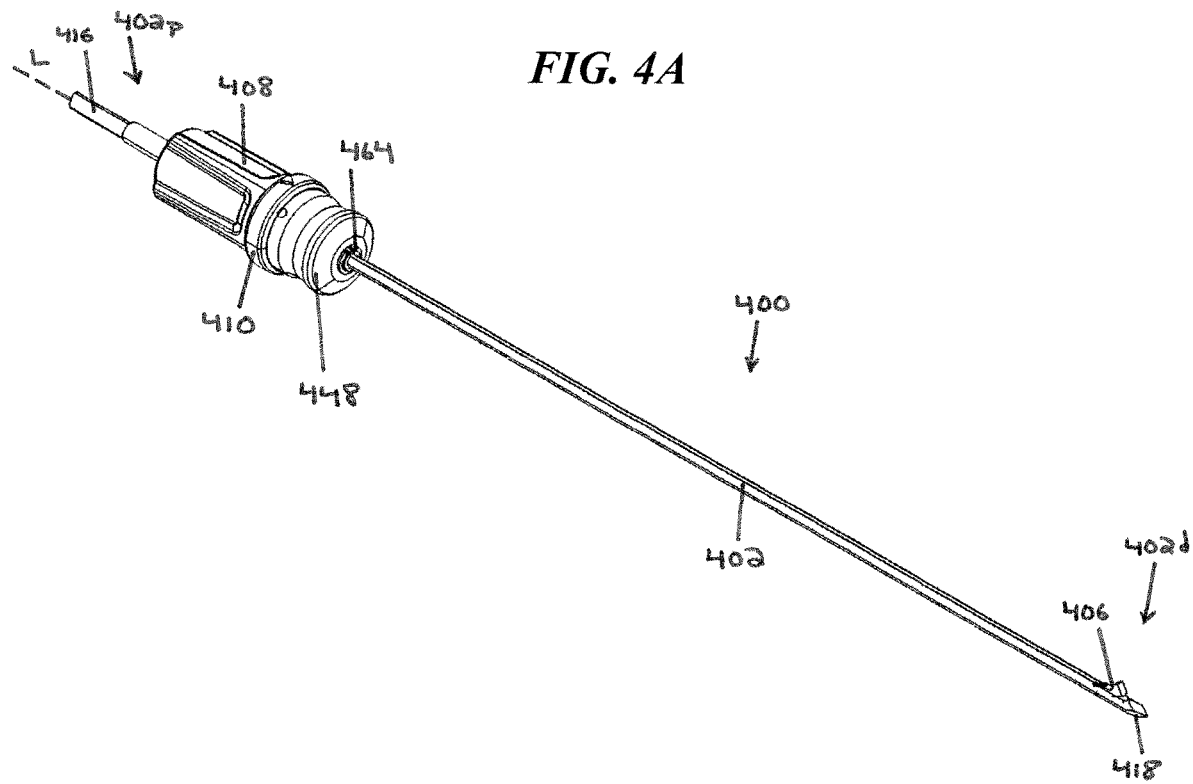
FIG. 4A is a perspective view of another exemplary embodiment of a cutting instrument.
Figure 4B:
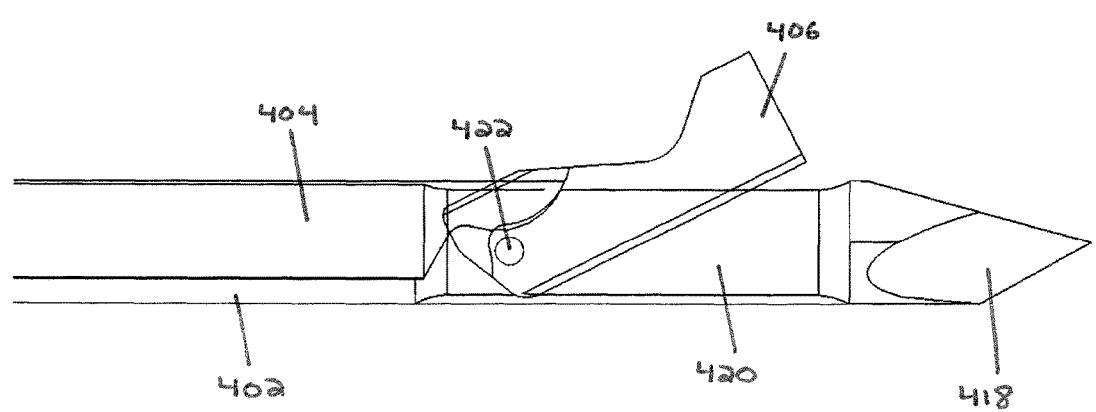
FIG. 4B is a sectional profile view of a distal end of the cutting instrument of FIG. 4A.

The proximal end of the body 402 defines a faceted mating interface or shank 416 for coupling to the chuck of a drill (e.g., an electric or pneumatic surgical drill). The distal end of the body 402 defines a sharpened tip 418 for cutting a hole in an object in an antegrade or forward direction. The tip 418 can have any of a variety of shapes or configurations, and can be optimized for forward cutting performance. The body 402 also includes a cavity 420 in which the cutting blade 406 is pivotally mounted via a cross pin 422. The cutting blade 406 can be selectively deployed or retracted through the opening of the cavity 420. In other words, the cutting blade 406 can be positioned in a deployed configuration, as shown in FIG. 4B, in which the blade protrudes through the opening, and a retracted configuration in which the blade does not protrude through the opening. The degree to which the blade 406 protrudes from the opening can be adjusted to adjust the diameter of the hole that is formed when the instrument 400 is used in a cutting operation. The cutting blade 406 can have any of a variety of shapes or configurations, and can be optimized for retrograde cutting and/or antegrade cutting performance.

The actuation shaft 404 extends through an inner lumen of the body 402 and is longitudinally-translatable relative to the body. The distal end of the actuation shaft 404 can be coupled to the cutting blade 406 in any of a variety of ways. For example, as shown in FIG. 4B, the distal end of the actuation shaft 404 defines a bayonet-shaped tip that is coupled to the cutting blade 406 (e.g., in the same manner as discussed above with respect to the instrument 200). In operation, proximal translation of the actuation shaft 404 relative to the body 402 causes the blade 406 to pivot about the cross pin 422 and to be deployed through the opening. The degree to which the actuation shaft 404 is translated proximally controls the degree to which the cutting blade 406 protrudes from the opening. Distal translation of the actuation shaft 404 relative to the body 402 causes the blade 406 to pivot in the opposite direction about the cross pin 422 and to be retracted into the cavity.

Figure 4C:
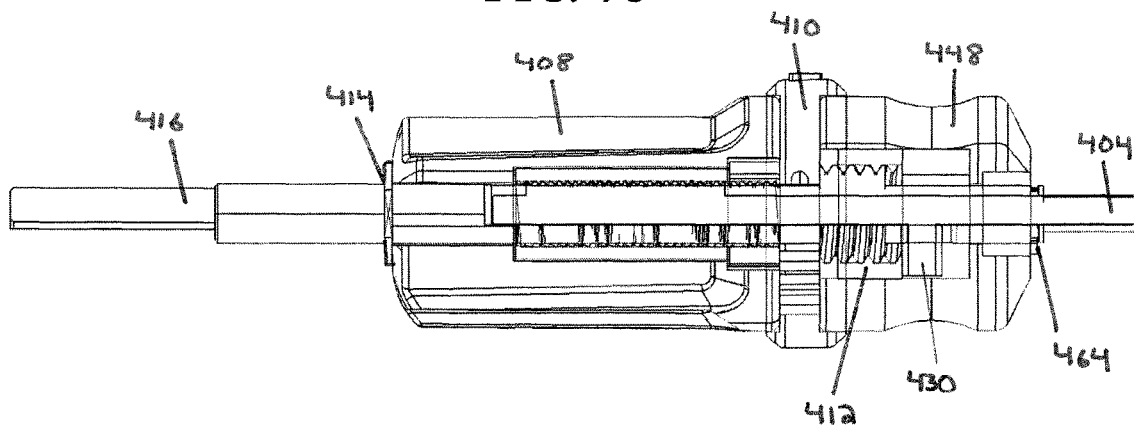
FIG. 4C is a sectional profile view of a proximal end of the cutting instrument of FIG. 4A.
Figure 4D:
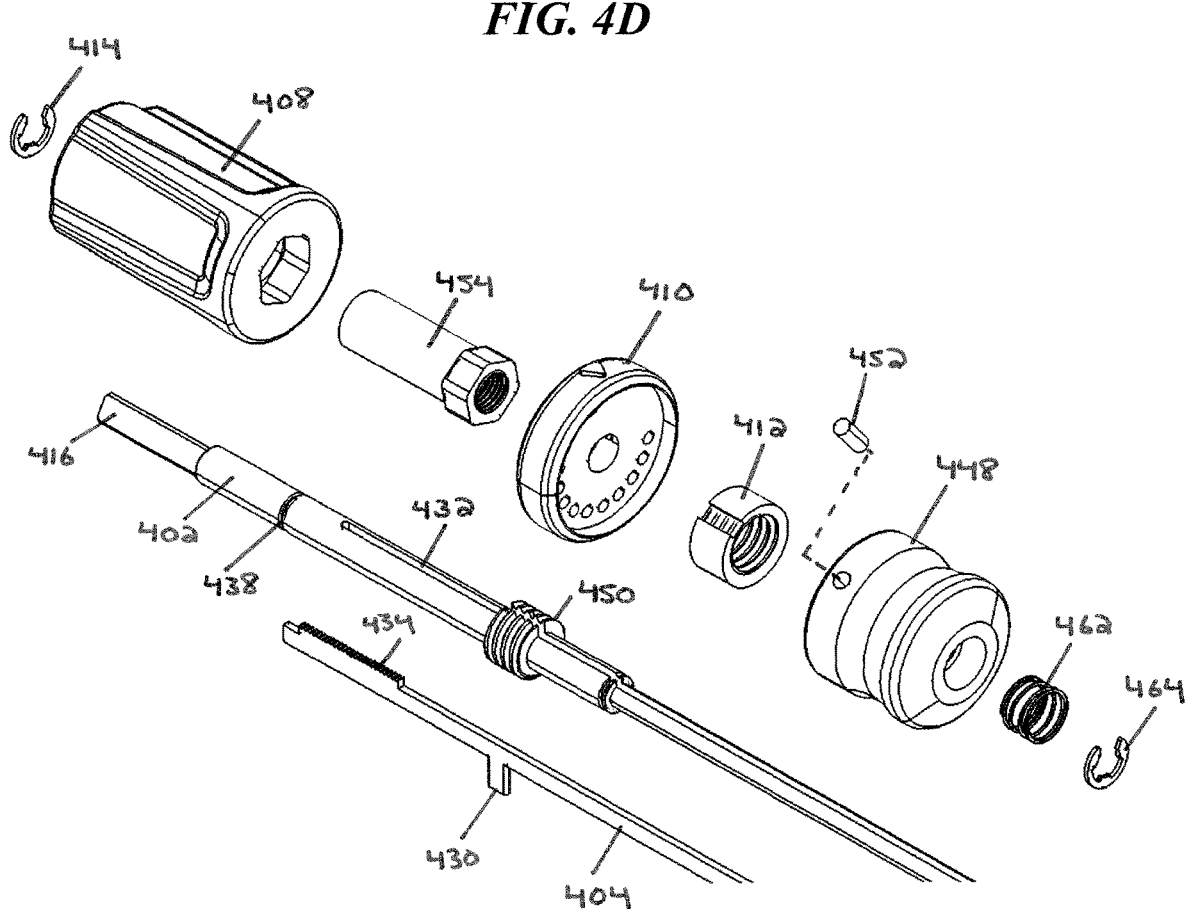
FIG. 4D is an exploded view of the proximal end of the cutting instrument of FIG. 4A.
Figure 4E:
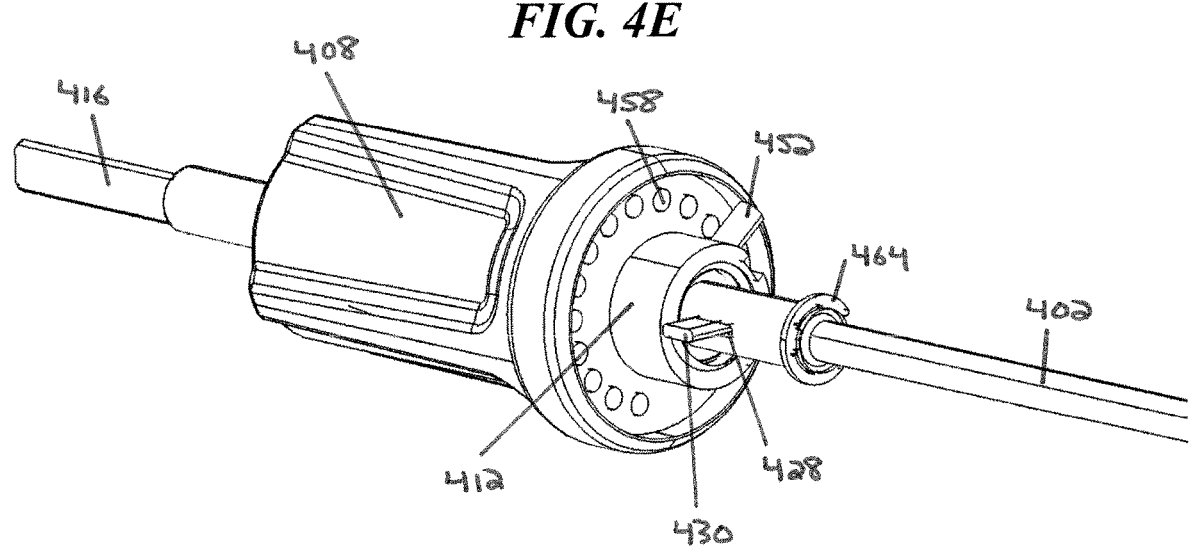
FIG. 4E is a perspective view of the proximal end of the cutting instrument of FIG. 4A shown with an adjustment knob and bias spring removed.

As shown in FIGS. 4C-4E, a cylindrical proximal portion of the body 402 defines a first longitudinal slot 428 in which a first tab portion 430 of the actuation shaft 404 is slidably positioned. The slot 428 has a length that is greater than the length of the tab 430, such that the tab can slide longitudinally within the slot between a proximal position in which the blade 406 is fully-deployed and a distal position in which the blade is fully-retracted. The length of the slot 428 thus defines the range of diameters to which the blade 406 can be deployed and therefore the range of tunnel diameters that can be formed by the blade. The stop ring 412 has a threaded interior surface that is threaded onto a threaded exterior portion 450 of the body 402. As shown in FIG. 4E, the stop ring 412 covers at least a proximal portion of the slot 428, such that the proximal travel limit of the tab 430 is defined by the stop ring. A cross-pin 452 fixes the rotational position of the adjustment knob 448 relative to the stop ring 412, such that rotation of the adjustment knob is effective to rotate the stop ring relative to the body 402. Such rotation causes the stop ring 412 to translate longitudinally along the body 402. Accordingly, rotating the adjustment knob 448 in a first direction about the longitudinal axis L advances the stop ring 412 distally to effectively reduce the length of the slot 428 and thus decrease the maximum cutting diameter. Rotating the adjustment knob 448 in a second, opposite direction about the longitudinal axis L retracts the stop ring 412 proximally to effectively increase the length of the slot 428 and thus increase the maximum cutting diameter.

The cylindrical proximal portion of the body 402 also defines a second longitudinal slot 432 in which a second tab portion 434 of the actuation shaft 404 is slidably positioned. The actuation knob 408 is rotatably positioned over the cylindrical proximal portion of the body 402 such that a threaded interior surface of an inner tube 454 mounted in the actuation knob engages a threaded surface of the second tab 434 of the actuation shaft 404.

The actuation knob 408 is sandwiched between a proximal retaining clip 414, which engages a groove 438 in the body 402, and the disc handle 410 to maintain the actuation knob at a fixed longitudinal position relative to the body 402. In operation, rotation of the actuation knob 408 relative to the body 402 and the handle portion 410 causes the threads of the actuation shaft 404 to ride along the threads of the actuation knob 408, thus causing the actuation shaft to translate longitudinally relative to the body. The proximal limit of this longitudinal translation is defined by the longitudinal position of the stop ring 412 over the first slot 428. The actuation knob 408 can be rotated in a first direction about the longitudinal axis L to pull the actuation shaft 404 proximally and deploy the blade 406 and/or increase the cutting diameter. The actuation knob 408 can also be rotated in a second, opposite direction about the longitudinal axis L to push the actuation shaft 404 distally and retract the blade 406 and/or decrease the cutting diameter.

Figure 4F:
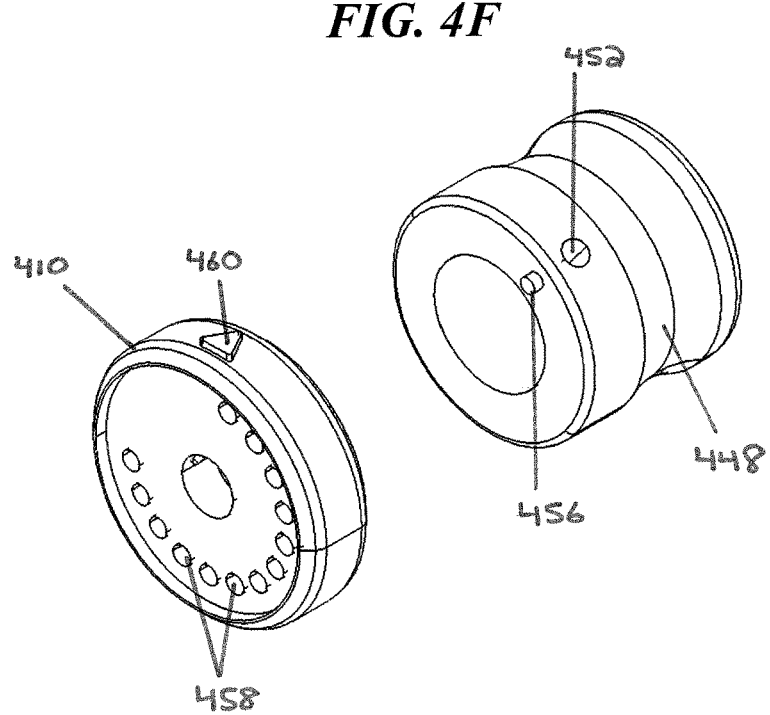
FIG. 4F is an exploded view of an adjustment knob and disc handle of the cutting instrument of FIG. 4A.

As noted above, the position of the stop ring 412 can be adjusted by rotating the adjustment knob 448 relative to the body 402 and the disc handle 410. As shown in FIGS. 4D-4F, the adjustment knob 448 includes a pin 456 that extends proximally from a proximal-facing end surface of the adjustment knob. The pin 456 can be received in any of a plurality of holes 458 formed in the disc handle 410. Each of the holes 458 is indexed to a predetermined cutting diameter (e.g., such that movement of the pin 456 from one hole to an adjacent hole results in a 0.5 mm increase or decrease in cutting diameter, depending on the direction of the adjacency). To adjust the diameter setting, the adjustment knob 448 can be urged distally to withdraw the pin 456 from the holes 458 in the disc handle 410. The adjustment knob 448 can then be rotated to the desired setting (which can be indicated by markings on the adjustment knob and an indicator arrow 460 on the disc handle 410). Finally, the adjustment knob 448 can be urged proximally such that the pin 456 engages one of the plurality of holes 458 formed in the disc handle 410. A bias spring 462 can be provided to urge the adjustment knob 448 in the proximal direction. When the pin 456 is seated in one of the holes 458, it prevents the adjustment knob 448 from being rotated, and ensures that the stop ring 412 will not inadvertently move. This ensures that the instrument 400 remains set to the desired diameter throughout the cutting operation. The bias spring 462 provides compression on the adjustment knob 448, keeping the pin 456 seated in the hole 458 until the user overcomes the spring force by pushing the adjustment knob distally. A distal c-clip 464 can be attached to the body 402 to provide a distal stop for the bias spring 462.

In an exemplary method of using the instrument 400, the instrument can be prepared for use by a surgical technician on a "back table" before handing the instrument to the surgeon or other user. This preparation can include setting the cutting diameter using the adjustment knob 448 as described above and rotating the actuation knob 408 to position the blade 406 in the fully-retracted position. When the surgeon is ready to form a stepped opening, the surgeon actuates a drill to which the instrument 400 is coupled to form the reduced diameter portion of the opening with the forward cutting tip 418. The surgeon then rotates the actuation knob 408 until further rotation is not possible, indicating that the blade 406 has been deployed to the pre-determined limit set by the surgical technician using the adjustment knob 448. The surgeon then actuates the drill to retro-cut the enlarged diameter portion of the stepped opening. Finally, the surgeon rotates the actuation handle 408 to return the cutting blade 406 to the fully-retracted position and withdraws the instrument 400 from the patient. Accordingly, the surgeon need not be concerned with setting the instrument 400 to the desired diameter while the instrument is in the patient. Rather, the desired diameter is pre-set and thus the surgeon can simply turn the actuation knob 408 until the stop ring 412 is engaged by the tab 430, reliably reaching the desired cutting diameter. In other words, the surgeon does not need to look at scales or calibrations when deploying the blade 406. The instrument 400 can also be used in other exemplary methods, as described further below.

FIGS. 5A-5F illustrate another exemplary embodiment of a cutting instrument 500.

As shown, the instrument 500 generally includes an elongate body 502 that extends from a proximal end 502p to a distal end 502d along a longitudinal axis L. The instrument 500 also includes an actuation shaft 504, a cutting blade 506, an actuation knob 508, a disc handle 510, a stop ring 512, and an adjustment knob 548.

Figure 5A:
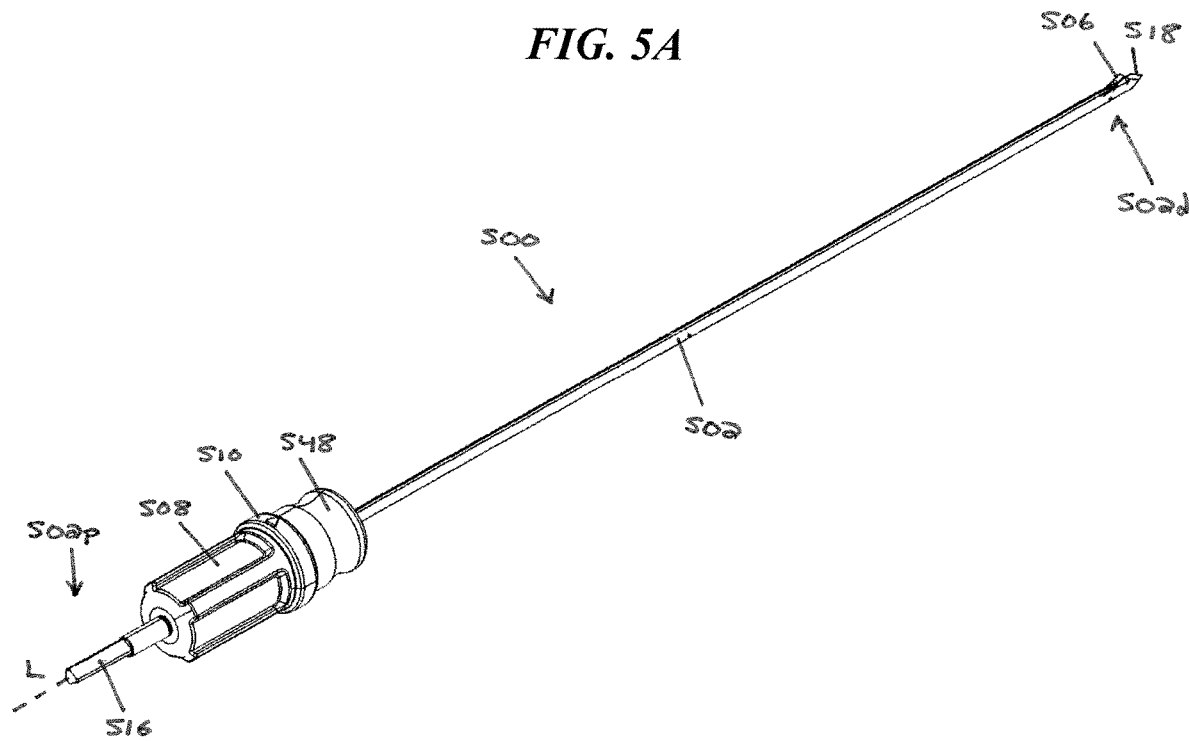
FIG. 5A is a perspective view of another exemplary embodiment of a cutting instrument.
Figure 5B:
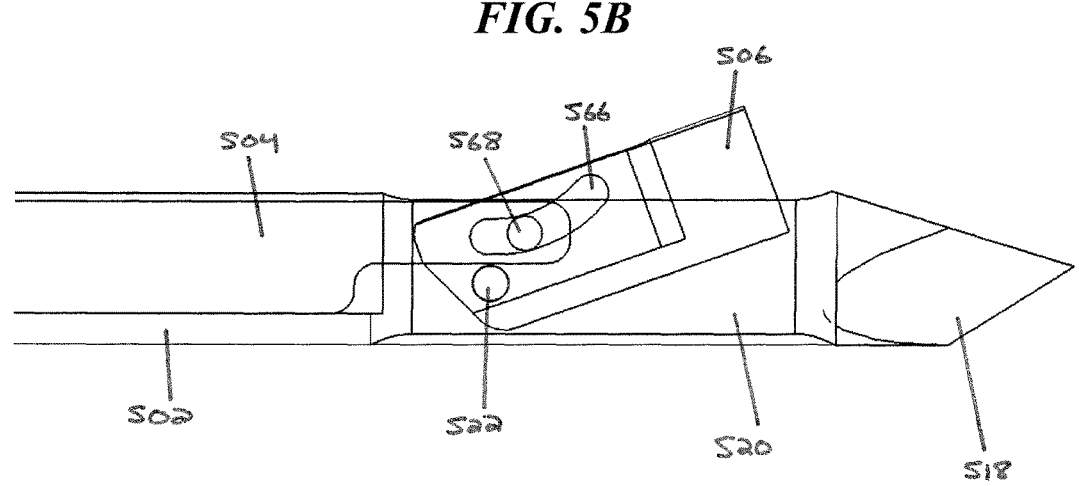
FIG. 5B is a sectional profile view of a distal end of the cutting instrument of FIG. 5A.

The proximal end of the body 502 defines a faceted mating interface or shank 516 for coupling to the chuck of a drill (e.g., an electric or pneumatic surgical drill). The distal end of the body 502 defines a sharpened tip 518 for cutting a hole in an object in an antegrade or forward direction. The tip 518 can have any of a variety of shapes or configurations, and can be optimized for forward cutting performance. The body 502 also includes a cavity 520 in which the cutting blade 506 is pivotally mounted via first and second side pins 522. The cutting blade 506 can be selectively deployed or retracted through the opening of the cavity 520. In other words, the cutting blade 506 can be positioned in a deployed configuration, as shown in FIG. 5B, in which the blade protrudes through the opening, and a retracted configuration in which the blade does not protrude through the opening. The degree to which the blade 506 protrudes from the opening can be adjusted to adjust the diameter of the hole that is formed when the instrument 500 is used in a cutting operation. The cutting blade 506 can have any of a variety of shapes or configurations, and can be optimized for retrograde cutting and/or antegrade cutting performance.

Figure 5C:
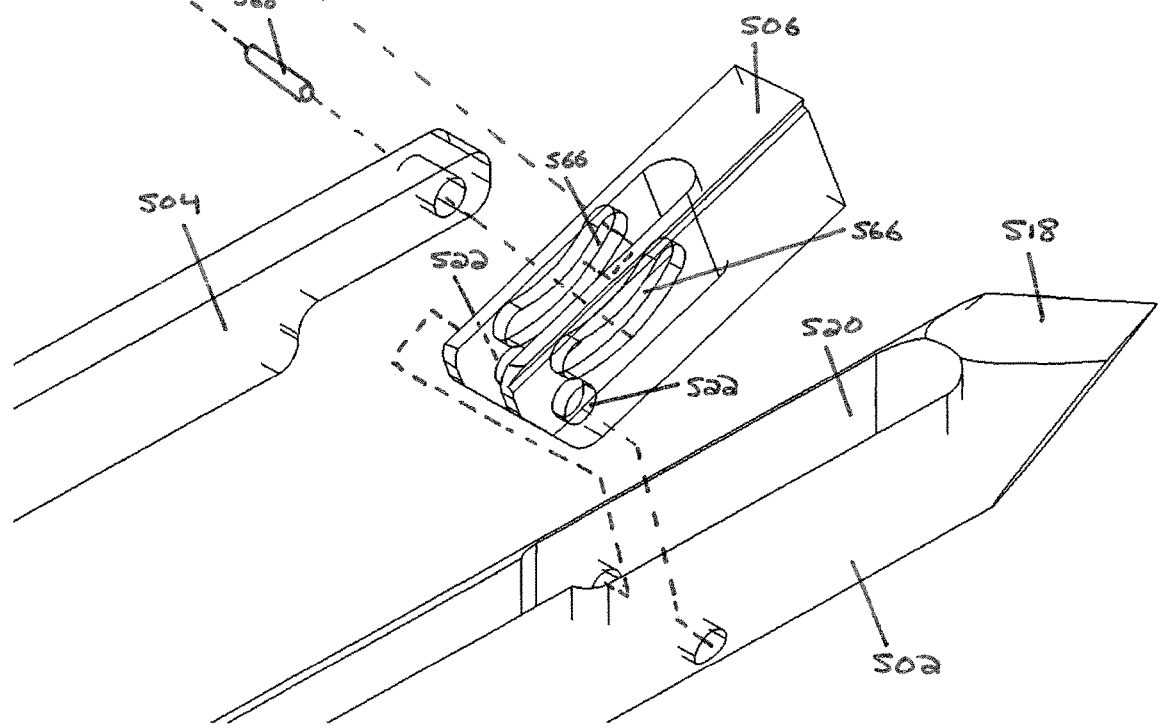
FIG. 5C is an exploded view of the distal end of the cutting instrument of FIG. 5A.

The actuation shaft 504 extends through an inner lumen of the body 502 and is longitudinally-translatable relative to the body. The distal end of the actuation shaft 504 can be coupled to the cutting blade 506 in any of a variety of ways. For example, the actuation shaft 504 can be coupled to the cutting blade 506 in the same manner as discussed above with respect to the instrument 200. FIGS. 5B-5C, however, illustrate an alternative mechanism for coupling the actuation shaft 504 to the cutting blade 506. It will be appreciated that the mechanism shown in FIGS. 5B-5C can be used with any of the cutting instruments 200, 300, 400 described above. As shown, the cutting blade 506 defines a proximal yoke portion in which the distal end of the actuation shaft 504 is received. Each fork of the yoke portion defines a curved cam slot 566. A cross-pin 568 extends through a hole formed in the distal end of the actuation shaft 504 and through each of the cam slots 566 of the cutting blade 506. In operation, proximal translation of the actuation shaft 504 relative to the body 502 causes the cross-pin 568 to slide along the cam slots 566, thereby causing the blade 506 to pivot about the first and second side pins 522 and to be deployed through the opening. The degree to which the actuation shaft 504 is translated proximally controls the degree to which the cutting blade 506 protrudes from the opening. Distal translation of the actuation shaft 504 relative to the body 502 causes the blade 506 to pivot in the opposite direction about the first and second side pins 522 and to be retracted into the cavity 520.

Figure 5D:
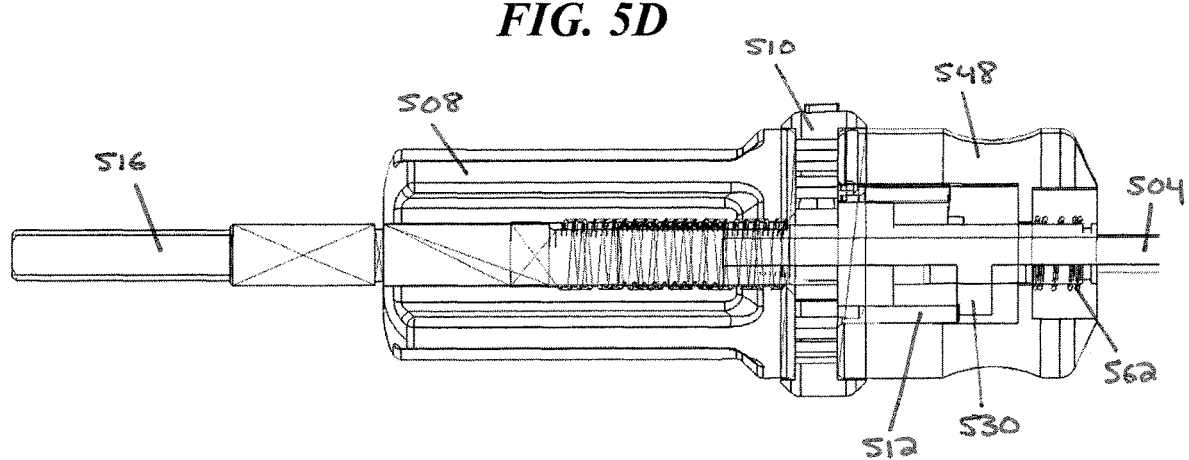
FIG. 5D is a sectional profile view of a proximal end of the cutting instrument of FIG. 5A.
Figure 5E:
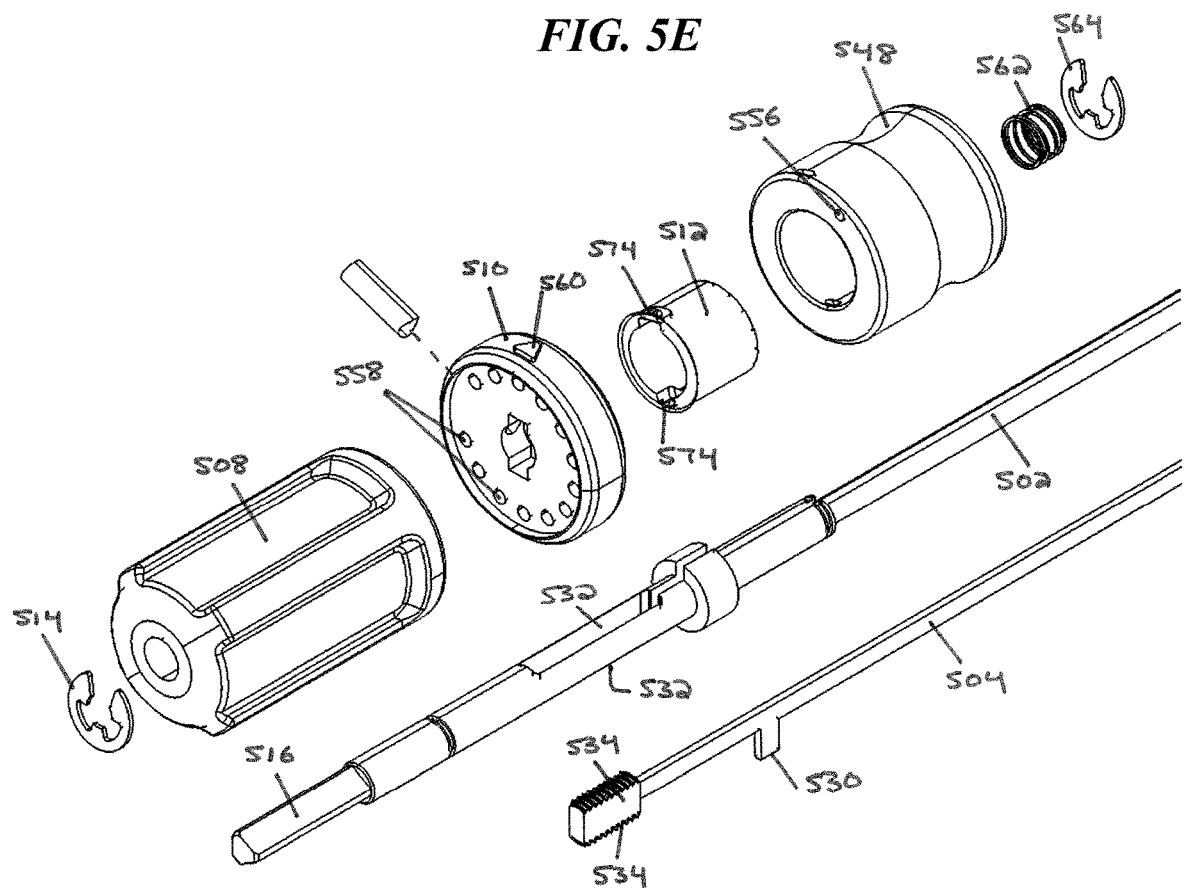
FIG. 5E is an exploded view of the proximal end of the cutting instrument of FIG. 5A.
Figure 5F:
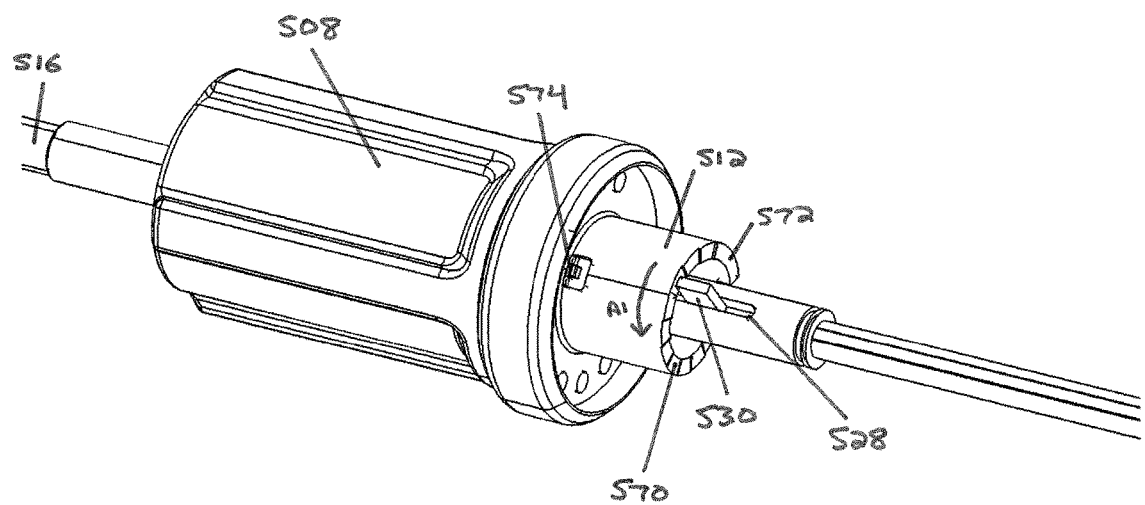
FIG. 5F is a perspective view of the proximal end of the cutting instrument of FIG. 5A shown with an adjustment knob and bias spring removed.

As shown in FIGS. 5D-5F, a cylindrical proximal portion of the body 502 defines a first longitudinal slot 528 in which a first tab portion 530 of the actuation shaft 504 is slidably positioned. The slot 528 has a length that is greater than the length of the tab 530, such that the tab can slide longitudinally within the slot between a proximal position in which the blade 506 is fully-deployed and a distal position in which the blade is fully-retracted. The length of the slot 528 thus defines the range of diameters to which the blade 506 can be deployed and therefore the range of tunnel diameters that can be formed by the blade. As shown in FIG. 5F, the stop ring 512 has a stepped distal-facing surface 570. Accordingly, the length of the stop ring 512 differs at each of a plurality of discrete radial positions about the circumference of the stop ring. As also shown in FIG. 5F, the stop ring 512 covers at least a proximal portion of the slot 528, such that the proximal travel limit of the tab 530 is defined by the stop ring. The effective length of the slot 528 can thus be changed by changing which step of the stop ring 512 is aligned with the slot. The illustrated stop ring 512 has a first step 572 at which the length of the stop ring is at its maximum. The length of the stop ring 512 is reduced at each successive step as one moves in the direction of the arrow A1. A pair of spring clips 574 fix the rotational position of the adjustment knob 548 relative to the stop ring 512, such that rotation of the adjustment knob is effective to rotate the stop ring relative to the body 502. Accordingly, rotating the adjustment knob 548 in a first direction about the longitudinal axis L aligns taller steps of the stop ring 512 with the slot 528 to effectively reduce the length of the slot and thus decrease the maximum cutting diameter. Rotating the adjustment knob 548 in a second, opposite direction about the longitudinal axis L aligns shorter steps of the stop ring 512 with the slot 528 to effectively increase the length of the slot and thus increase the maximum cutting diameter.

In some instances, it can be easier to control the tolerances of a stepped stop ring of the type used in the instrument 500 as compared with other types of stop rings such as the threaded stop ring of the instrument 400. The stepped stop ring can thus provide, in some instances, more uniform rotation and easier calibration.

The cylindrical proximal portion of the body 502 also defines upper and lower second longitudinal slots 532 in which upper and lower second tab portions 534 of the actuation shaft 504 are slidably positioned. The actuation knob 508 is rotatably positioned over the cylindrical proximal portion of the body 502 such that a threaded interior surface of the actuation knob engages threaded surfaces of the upper and lower second tabs 534 of the actuation shaft 504.

The actuation knob 508 is sandwiched between a proximal retaining clip 514 and the disc handle 510 to maintain the actuation knob at a fixed longitudinal position relative to the body 502. In operation, rotation of the actuation knob 508 relative to the body 502 and the handle portion 510 causes the threads of the actuation shaft 504 to ride along the threads of actuation knob, thus causing the actuation shaft to translate longitudinally relative to the body. The proximal limit of this longitudinal translation is defined by which step of the stop ring 512 is positioned over the first slot 528. The actuation knob 508 can be rotated in a first direction about the longitudinal axis L to pull the actuation shaft 504 proximally and deploy the blade 506 and/or increase the cutting diameter. The actuation knob 508 can also be rotated in a second, opposite direction about the longitudinal axis L to push the actuation shaft 504 distally and retract the blade 506 and/or decrease the cutting diameter.

As noted above, the position of the stop ring 512 can be adjusted by rotating the adjustment knob 548 relative to the body 502 and the disc handle 510. As shown in FIG. 5E, the adjustment knob 548 includes a pin 556 that extends proximally from a proximal-facing end surface of the adjustment knob. The pin 556 can be received in any of a plurality of holes 558 formed in the disc handle 510. Each of the holes 558 is indexed to a predetermined cutting diameter (e.g., such that movement of the pin 556 from one hole to an adjacent hole results in a 0.5 mm increase or decrease in cutting diameter depending on the direction of the adjacency). To adjust the diameter setting, the adjustment knob 548 can be urged distally to withdraw the pin 556 from the holes 558 in the disc handle 510. The adjustment knob 548 can then be rotated to the desired setting (which can be indicated by markings on the adjustment knob and an indicator arrow 560 on the disc handle 510). Finally, the adjustment knob 548 can be urged proximally such that the pin 556 engages one of the plurality of holes 558 formed in the disc handle 510. A bias spring 562 can be provided to urge the adjustment knob 548 in the proximal direction. When the pin 556 is seated in one of the holes 558, it prevents the adjustment knob 548 from being rotated, and ensures that the stop ring 5112 will not inadvertently move. This ensures that the instrument 500 remains set to the desired diameter throughout the cutting operation. The bias spring 562 provides compression on the adjustment knob 548, keeping the pin 556 seated in the hole 558 until the user overcomes the spring force by pushing the adjustment knob distally. A distal c-clip 564 can be attached to the body 502 to provide a distal stop for the bias spring 562.

In an exemplary method of using the instrument 500, the instrument can be prepared for use by a surgical technician on a "back table" before handing the instrument to the surgeon. This preparation can include setting the retro-cutting diameter using the adjustment knob 548 as described above and rotating the actuation handle 508 to position the blade 506 in the fully-retracted position. When the surgeon is ready to form a stepped opening, the surgeon actuates a drill to which the instrument 500 is coupled to form the reduced diameter portion of the opening with the forward cutting tip 518. The surgeon then rotates the actuation handle 508 until further rotation is not possible, indicating that the blade 506 has been deployed to the pre-determined limit set by the surgical technician using the adjustment knob 548. The surgeon then actuates the drill to retro-cut the enlarged diameter portion of the stepped opening. Finally, the surgeon rotates the actuation handle 508 to return the cutting blade 506 to the fully-retracted position and withdraws the instrument 500 from the patient. Accordingly, the surgeon need not be concerned with setting the instrument 500 to the desired diameter while the instrument is in the patient. Rather, the desired diameter is pre-set and thus the surgeon can simply turn the actuation knob 508 until the stop ring 512 is engaged by the tab 530, reliably reaching the desired cutting diameter. In other words, the surgeon does not need to look at scales or calibrations when deploying the blade 506. The instrument 500 can also be used in other exemplary methods, as described further below.

FIGS. 6A-6F illustrate another exemplary embodiment of a cutting instrument 600.

As shown, the instrument 600 generally includes an elongate body 602 that extends from a proximal end 602p to a distal end 602d along a longitudinal axis L. The instrument 600 also includes an actuation shaft 604, a cutting blade 606, an actuation knob 608, an adjustment ring 648 with a stepped stop surface 670, and a forward handle 610.

The proximal end of the body 602 defines a faceted mating interface or shank 616 for coupling to the chuck of a drill (e.g., an electric or pneumatic surgical drill). The distal end of the body 602 defines a sharpened tip 618 for cutting a hole in an object in an antegrade or forward direction. The tip 618 can have any of a variety of shapes or configurations, and can be optimized for forward cutting performance. The body 602 also includes a cavity 620 in which the cutting blade 606 is pivotally mounted via a cross pin 622. The cutting blade 606 can be selectively deployed or retracted through the opening of the cavity 620. In other words, the cutting blade 606 can be positioned in a deployed configuration in which the blade protrudes through the opening, and a retracted configuration in which the blade does not protrude through the opening. The degree to which the blade 606 protrudes from the opening can be adjusted to adjust the diameter of the hole that is formed when the instrument 600 is used in a cutting operation. The cutting blade 606 can have any of a variety of shapes or configurations, and can be optimized for retrograde cutting and/or antegrade cutting performance.

Figure 6A:
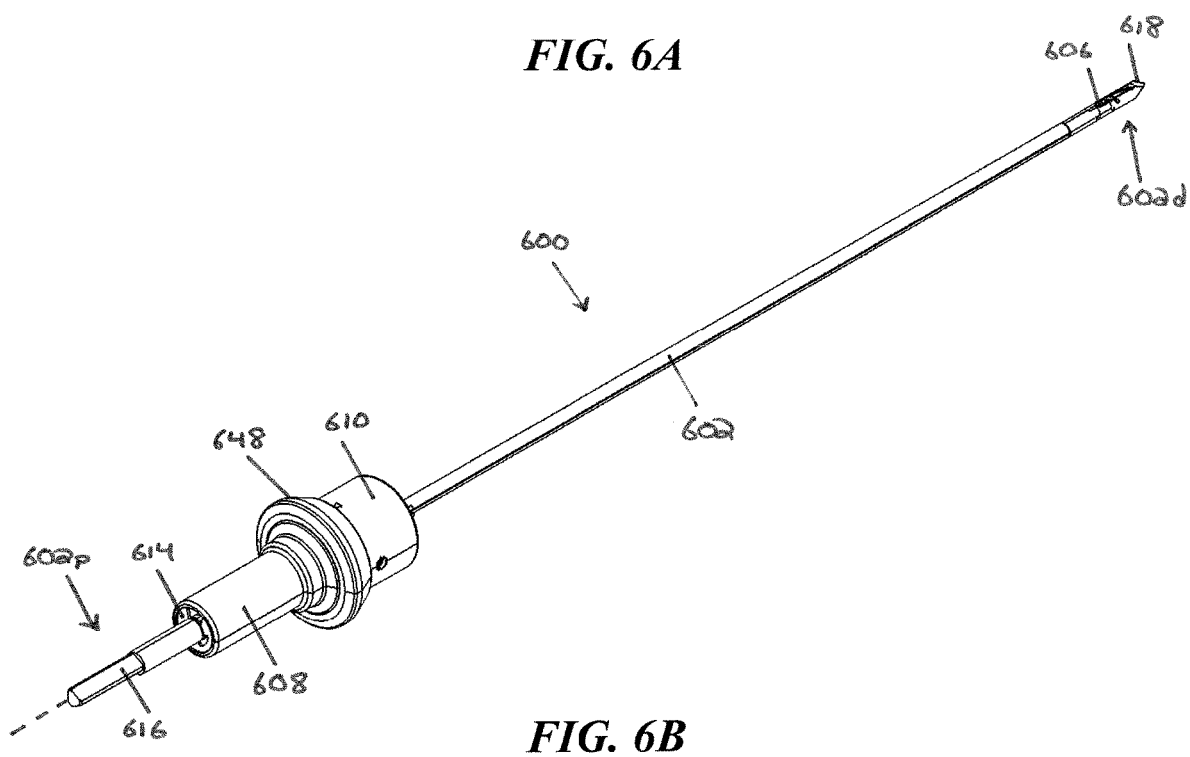
FIG. 6A is a perspective view of another exemplary embodiment of a cutting instrument.
Figure 6B:
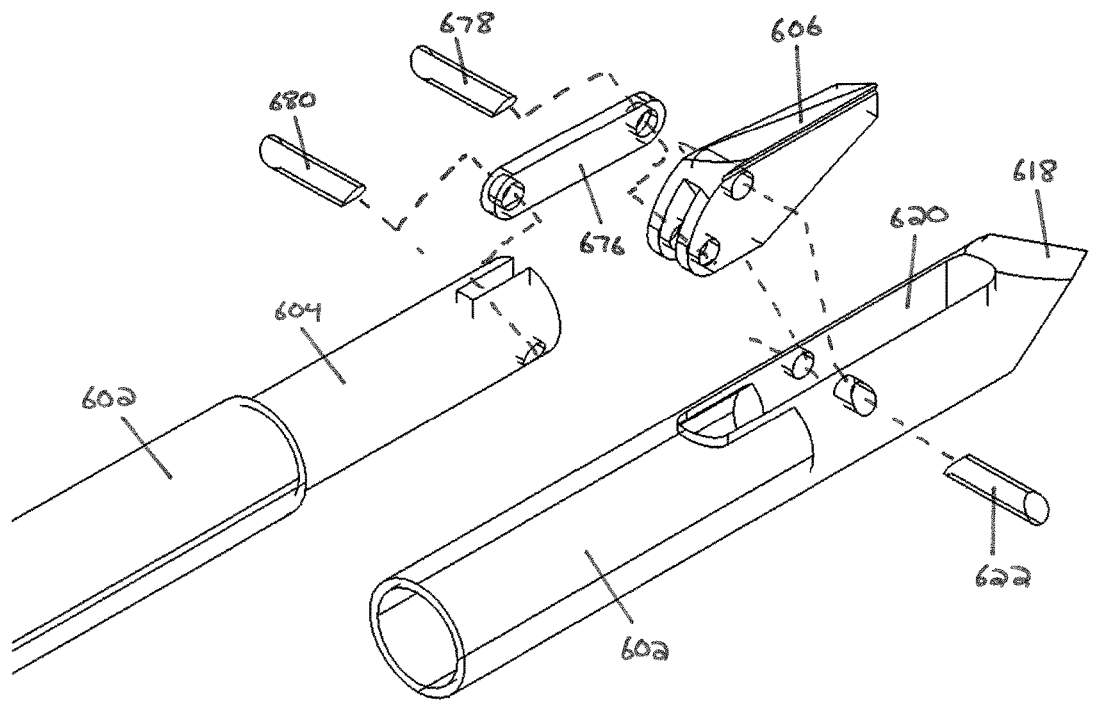
FIG. 6B is an exploded view of a distal end of the cutting instrument of FIG. 6A.
Figure 6C:
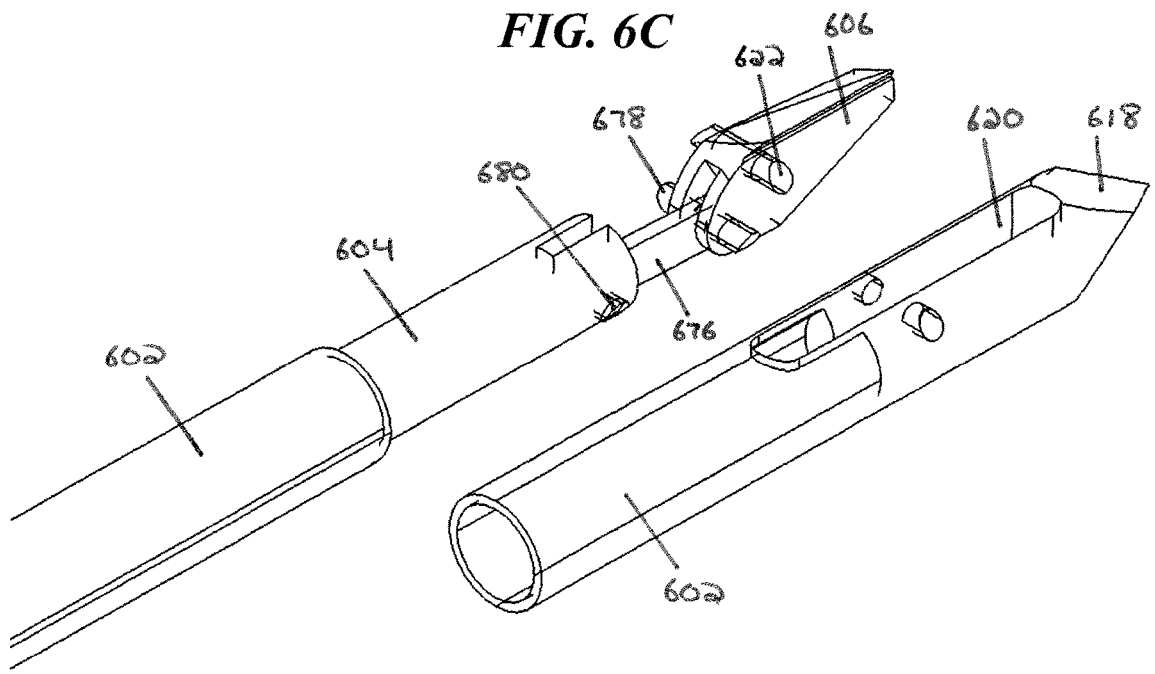
FIG. 6C is a partially-exploded view of the distal end of the cutting instrument of FIG. 6A.

The actuation shaft 604 extends through an inner lumen of the body 602 and is longitudinally-translatable relative to the body. The actuation shaft 604 can be a solid cylindrical rod, which can advantageously provide additional strength and rigidity and reduced deformation during use. The distal end of the actuation shaft 604 can be coupled to the cutting blade 606 in any of a variety of ways. For example, as shown in FIGS. 6B-6C, a linkage assembly can be used to couple the actuation shaft 604 to the cutting blade 606. As shown, the cutting blade 606 defines a proximal yoke portion in which a distal end of a link bar 676 is received. The distal end of the link bar 676 is coupled to the cutting blade 606 by a first pivot pin 678. The proximal end of the link bar 676 is received in a yoke formed in the distal end of the actuation shaft 604 and is coupled thereto by a second pivot pin 680. The link bar 676 is coupled to the blade 606 at a position offset from the cross pin 622, such that longitudinal translation of the link bar causes the blade to rotate about the cross pin. In operation, proximal translation of the actuation shaft 604 relative to the body 602 pulls the link bar 676 in a proximal direction, causing the blade 606 to rotate about the cross pin 622 to the retracted position. Distal translation of the actuation shaft 604 relative to the body 602 pushes the link bar 676 in a distal direction, causing the blade 606 to rotate about the cross pin 622 to the deployed position. The degree to which the actuation shaft 604 is translated distally controls the degree to which the cutting blade 606 protrudes from the opening. A linkage of the type shown can advantageously provide a stiffer blade mechanism with little or no play in the blade as it is deployed and used in a cutting operation. Also, the illustrated cylindrical openings through which the first and second pivot pins 678, 680 are inserted can be easier to manufacture with precise tolerances than elongated cam slots or other mating features. Further, in the illustrated embodiment, pressure on the blade 606 when the blade is used for retrograde cutting tends to urge the actuation shaft 604 proximally. This urging is resisted by the threaded engagement between the actuation shaft 604 and the actuation knob 608, which provides a solid engagement to reduce or eliminate play in the blade 606 during cutting.

Figure 6D:
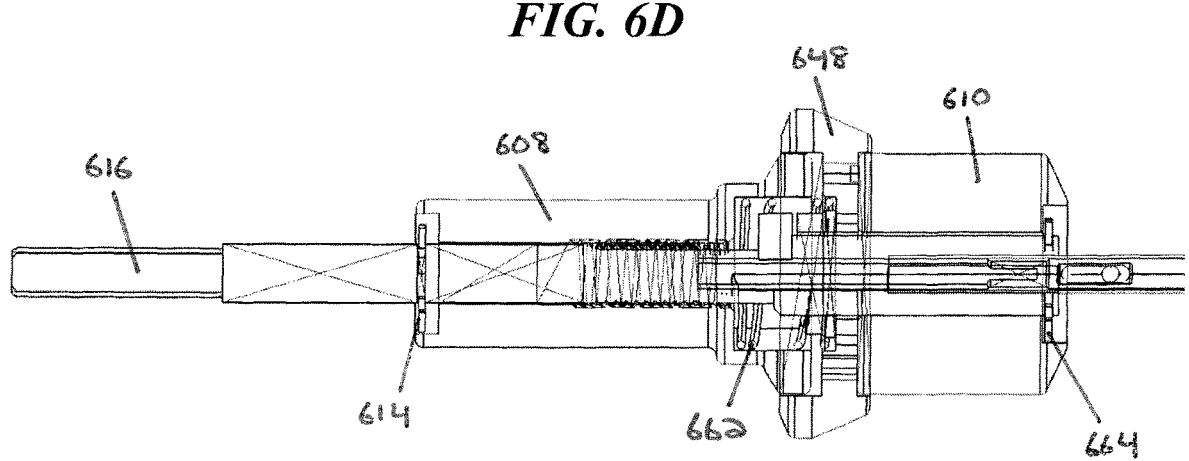
FIG. 6D is a sectional profile view of a proximal end of the cutting instrument of FIG. 6A.
Figure 6E:
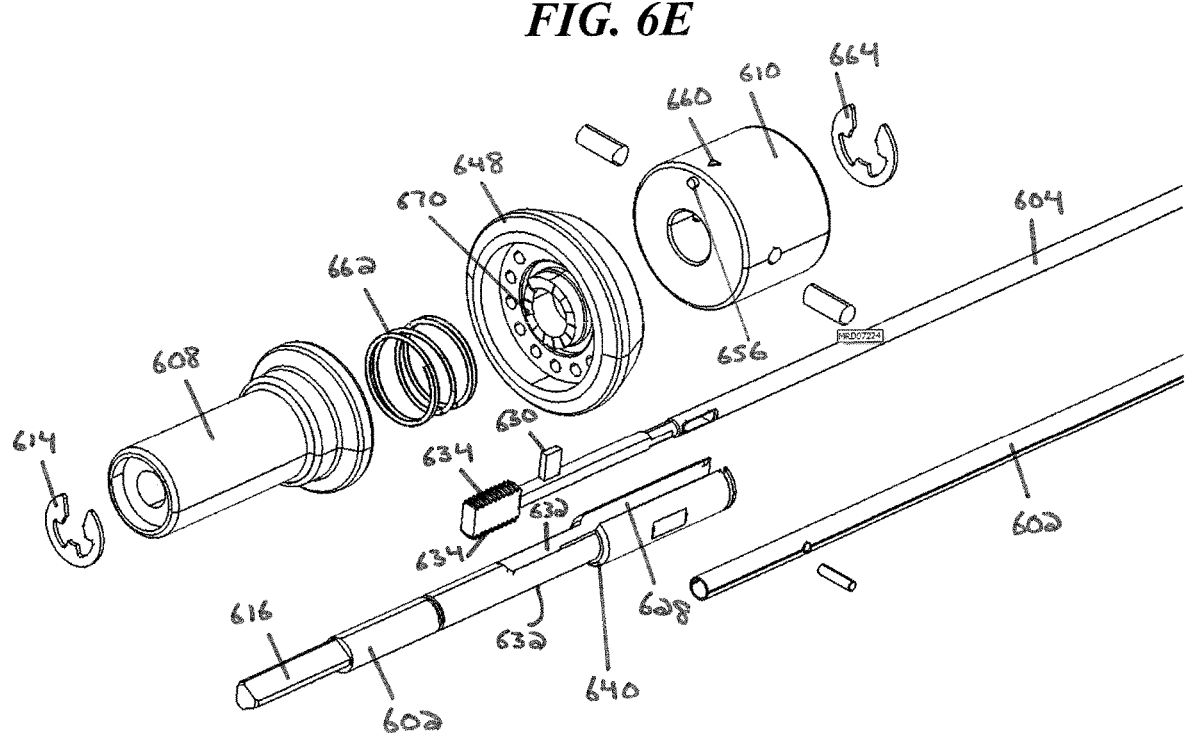
FIG. 6E is an exploded view of the proximal end of the cutting instrument of FIG. 6A.
Figure 6F:
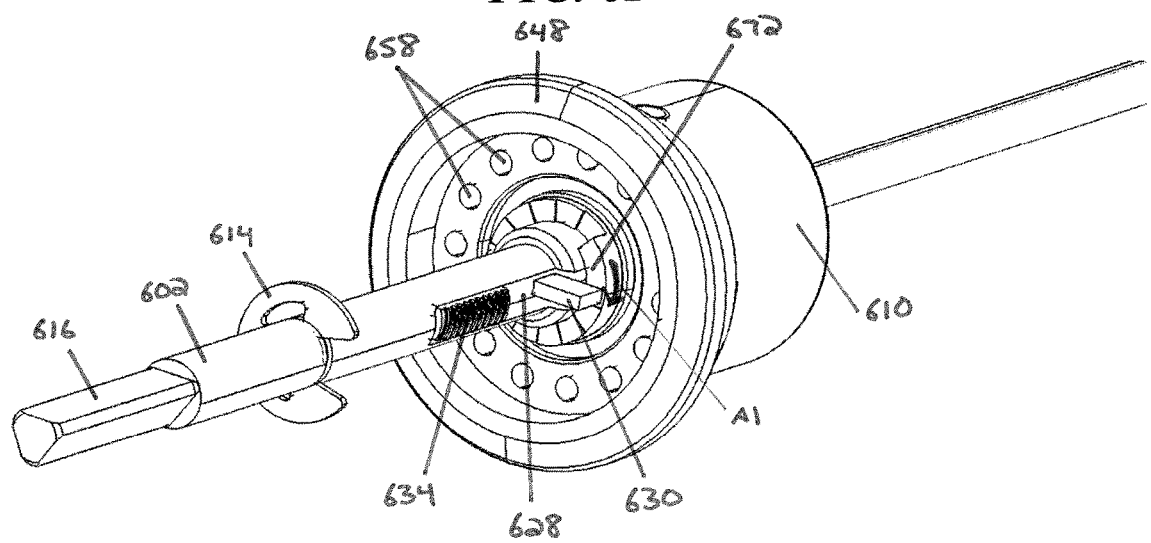
FIG. 6F is a perspective view of the proximal end of the cutting instrument of FIG. 6A shown with an actuation knob and bias spring removed.

As shown in FIGS. 6D-6F, a cylindrical proximal portion of the body 602 defines a first longitudinal slot 628 in which a first tab portion 630 of the actuation shaft 604 is slidably positioned. The slot 628 has a length that is greater than the length of the tab 630, such that the tab can slide longitudinally within the slot between a proximal position in which the blade 606 is fully-retracted and a distal position in which the blade is fully-deployed. The length of the slot 628 thus defines the range of diameters to which the blade 606 can be deployed and therefore the range of tunnel diameters that can be formed by the blade. As shown in FIG. 6E, the adjustment ring 648 includes a proximal-facing stepped stop surface 670. Accordingly, the length of the adjustment ring 648 differs at each of a plurality of discrete radial positions about the circumference of the stop surface 670. As shown in FIG. 6F, the adjustment ring 648 covers at least a distal portion of the slot 628, such that the distal travel limit of the tab 630 is defined by the stop surface 670. The effective length of the slot 628 can thus be changed by changing which step of the stop surface 670 is aligned with the slot. The illustrated stop surface 670 has a first step 672 at which the length of the adjustment ring 648 is at its maximum. The length of the adjustment ring 648 is reduced at each successive step as one moves in the direction of the arrow A1. Rotating the adjustment ring 648 in a first direction about the longitudinal axis L aligns taller steps of the stop surface 670 with the slot 628 to effectively reduce the length of the slot and thus decrease the maximum cutting diameter. Rotating the adjustment ring 648 in a second, opposite direction about the longitudinal axis L aligns shorter steps of the stop surface 670 with the slot 628 to effectively increase the length of the slot and thus increase the maximum cutting diameter.

The cylindrical proximal portion of the body 602 also defines upper and lower second longitudinal slots 632 in which upper and lower second tab portions 634 of the actuation shaft 604 are slidably positioned. The actuation knob 608 is rotatably positioned over the cylindrical proximal portion of the body 602 such that a threaded interior surface of the actuation knob engages threaded surfaces of the upper and lower second tabs 634 of the actuation shaft 604.

The actuation knob 608 is sandwiched between a proximal retaining clip 614 and a shoulder 640 of the body 602 to maintain the actuation knob at a fixed longitudinal position relative to the body. In operation, rotation of the actuation knob 608 relative to the body 602 and the forward handle portion 610 (which is pinned to the body to prevent rotation of the handle portion relative to the body) causes the threads of the actuation shaft 604 to ride along the threads of actuation knob, thus causing the actuation shaft to translate longitudinally relative to the body. The distal limit of this longitudinal translation is defined by which step of the stop surface 670 is aligned with the first slot 628. The actuation knob 608 can be rotated in a first direction about the longitudinal axis L to pull the actuation shaft 604 proximally and retract the blade 606 and/or decrease the cutting diameter. The actuation knob 608 can also be rotated in a second, opposite direction about the longitudinal axis L to push the actuation shaft 604 distally and deploy the blade 606 and/or increase the cutting diameter.

As noted above, the position of the stop surface 670 can be adjusted by rotating the adjustment ring 648 relative to the body 602 and the forward handle 610. As shown in FIG. 6E, the handle 610 includes a pin 656 that extends proximally from a proximal-facing end surface of the handle. The pin 656 can be received in any of a plurality of holes 658 formed in the adjustment ring 648. Each of the holes 658 is indexed to a predetermined cutting diameter (e.g., such that movement of the pin 656 from one hole to an adjacent hole results in a 0.5 mm increase or decrease in cutting diameter depending on the direction of the adjacency). To adjust the diameter setting, the adjustment ring 648 can be urged proximally to withdraw the pin 656 from the holes 658 in the adjustment ring. The adjustment ring 648 can then be rotated to the desired setting (which can be indicated by markings on the adjustment ring and an indicator arrow 660 on the forward handle 610). Finally, the adjustment ring 648 can be urged distally such that the pin 656 engages one of the plurality of holes 658 formed in the adjustment ring. A bias spring 662 can be provided to urge the adjustment ring 648 in the distal direction.

In an exemplary method of using the instrument 600, the instrument can be prepared for use by a surgical technician on a "back table" before handing the instrument to the surgeon. This preparation can include setting the retro-cutting diameter using the adjustment ring 648 as described above and rotating the actuation handle 608 to position the blade 606 in the fully-retracted position. When the surgeon is ready to form a stepped opening, the surgeon actuates a drill to which the instrument 600 is coupled to form the reduced diameter portion of the opening with the forward cutting tip 618. The surgeon then rotates the actuation handle 608 until further rotation is not possible, indicating that the blade 606 has been deployed to the pre-determined limit set by the surgical technician using the adjustment ring 648. The surgeon then actuates the drill to retro-cut the enlarged diameter portion of the stepped opening. Finally, the surgeon rotates the actuation handle 608 to return the cutting blade 606 to the fully-retracted position and withdraws the instrument 600 from the patient. Accordingly, the surgeon need not be concerned with setting the instrument 600 to the desired diameter while the instrument is in the patient. Rather, the desired diameter is pre-set and thus the surgeon can simply turn the actuation knob 608 until the stop 670 is engaged by the tab 630, reliably reaching the desired cutting diameter. In other words, the surgeon does not need to look at scales or calibrations when deploying the blade 606. The instrument 600 can also be used in other exemplary methods, as described further below.

FIGS. 7A-7G illustrate another exemplary embodiment of a cutting instrument 700.

As shown, the instrument 700 generally includes an elongate body 702 that extends from a proximal end 702*p* to a distal end 702*d* along a longitudinal axis L. The instrument 700 also includes an actuation shaft 704, a cutting blade 706, an actuation knob 708 with a torque limiter 782, an adjustment ring 748 with a stepped stop surface 770, and a forward handle 710.

The proximal end of the body 702 defines a faceted mating interface or shank 716 for coupling to the chuck of a drill (e.g., an electric or pneumatic surgical drill). The distal end of the body 702 defines a sharpened tip 718 for cutting a hole in an object in an antegrade or forward direction. The tip 718 can have any of a variety of shapes or configurations, and can be optimized for forward cutting performance. The body 702 also includes a cavity 720 in which the cutting blade 706 is pivotally mounted via a cross pin 722. The cutting blade 706 can be selectively deployed or retracted through the opening of the cavity 720. In other words, the cutting blade 706 can be positioned in a deployed configuration in which the blade protrudes through the opening, and a retracted configuration in which the blade does not protrude through the opening. The degree to which the blade 706 protrudes from the opening can be adjusted to adjust the diameter of the hole that is formed when the instrument 700 is used in a cutting operation. The cutting blade 706 can have any of a variety of shapes or configurations, and can be optimized for retrograde cutting and/or antegrade cutting performance.

The actuation shaft 704 extends through an inner lumen of the body 702 and is longitudinally-translatable relative to the body. The actuation shaft 704 can be a solid cylindrical rod, which can advantageously provide additional strength and rigidity and reduced deformation during use. The distal end of the actuation shaft 704 can be coupled to the cutting blade 706 in any of a variety of ways. For example, the actuation shaft 704 can have a distal end which is coupled to the cutting blade 706 by a linkage assembly as described above with respect to the instrument 600. In operation, proximal translation of the actuation shaft 704 relative to the body 702 pulls the blade 706 in a proximal direction, causing the blade to rotate about the cross pin 722 to the retracted position. Distal translation of the actuation shaft 704 relative to the body 702 pushes the blade 706 in a distal direction, causing the blade to rotate about the cross pin 722 to the deployed position. The degree to which the actuation shaft 704 is translated distally controls the degree to which the cutting blade 706 protrudes from the opening.

Figure 7A:
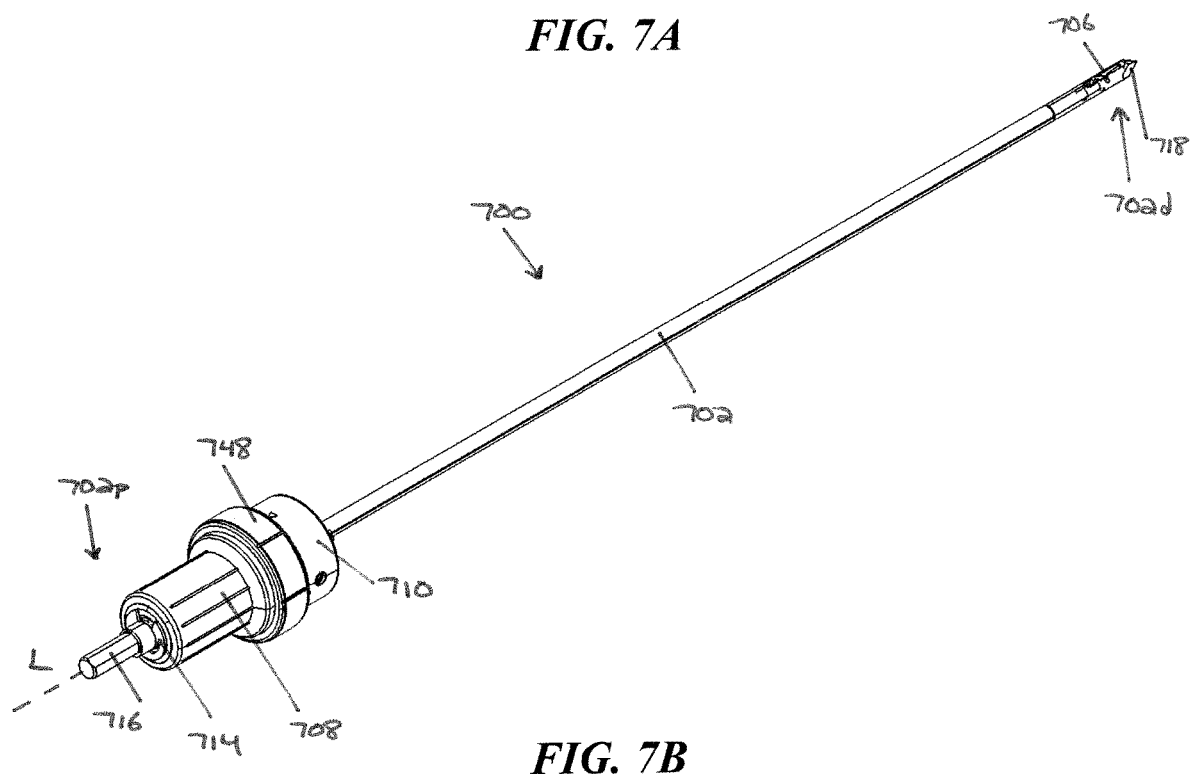
FIG. 7A is a perspective view of another exemplary embodiment of a cutting instrument.
Figure 7B:
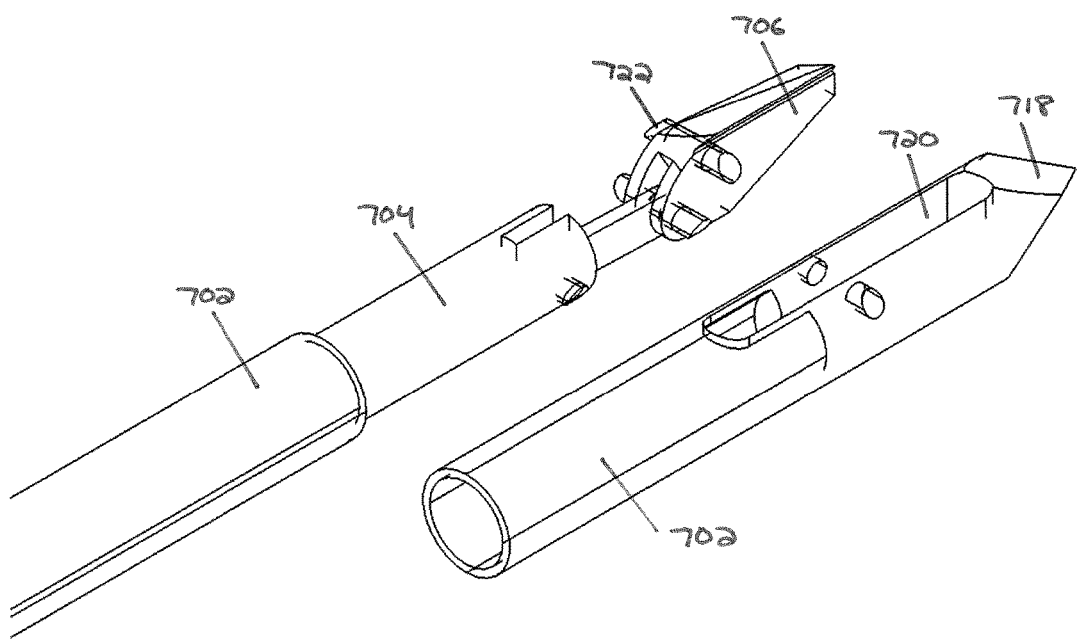
FIG. 7B is a partially-exploded view of the distal end of the cutting instrument of FIG. 7A.
Figure 7C:
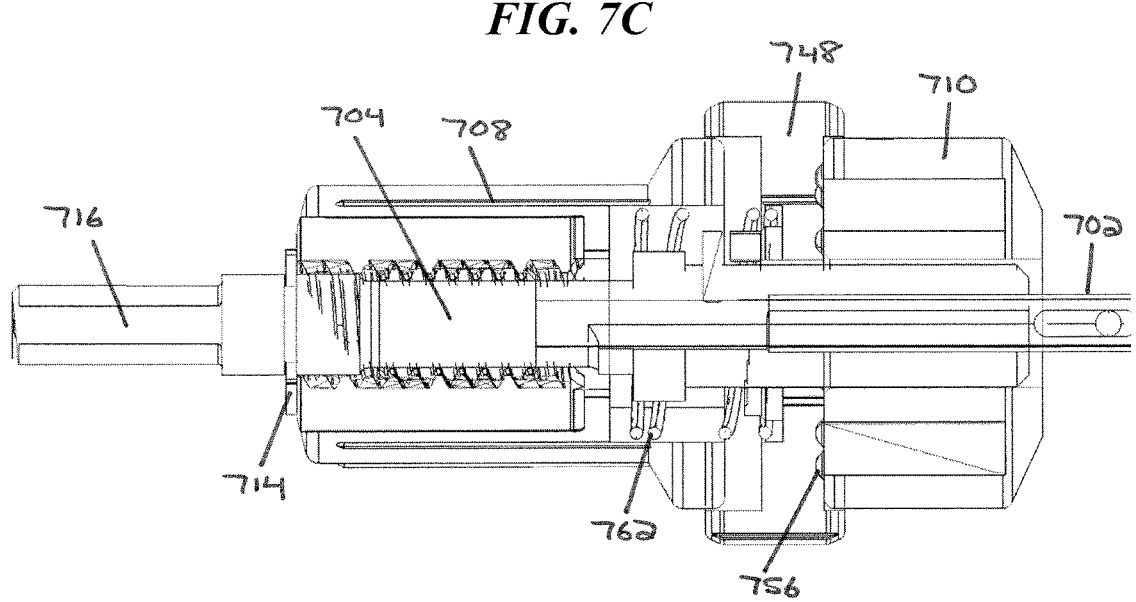
FIG. 7C is a sectional profile view of a proximal end of the cutting instrument of FIG. 7A.
Figure 7D:
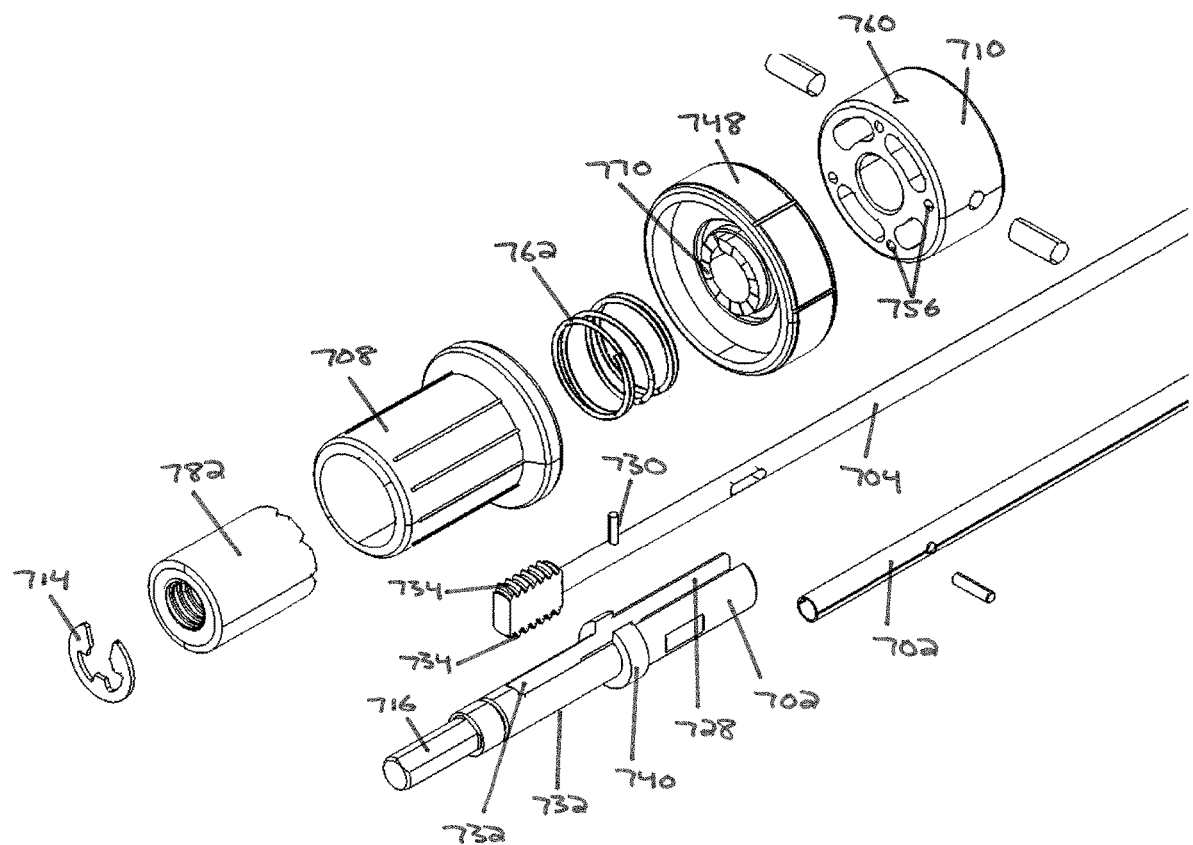
FIG. 7D is an exploded view of the proximal end of the cutting instrument of FIG. 7A.
Figure 7E:
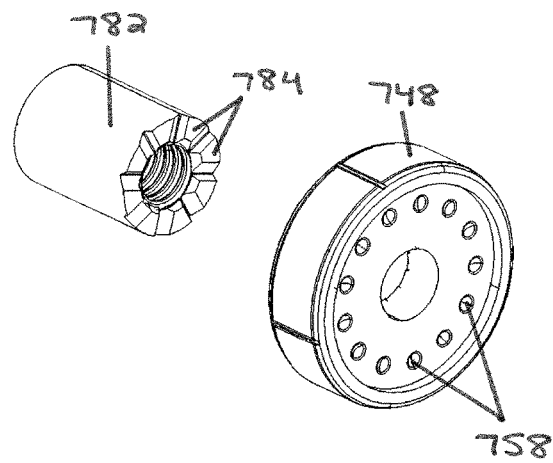
FIG. 7E is a perspective view of a torque limiter and adjustment ring of the cutting instrument of FIG. 7A.
Figure 7F:
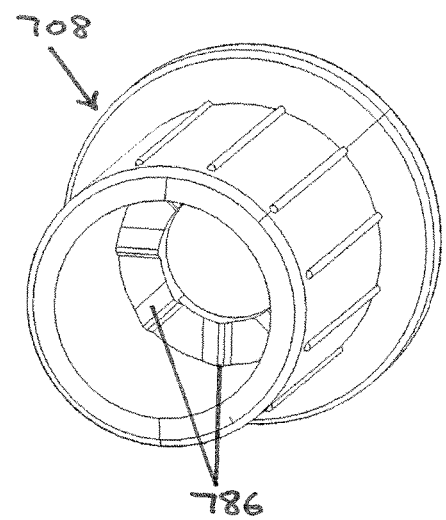
FIG. 7F is a perspective view of the actuation knob of the cutting instrument of FIG. 7A.
Figure 7G:
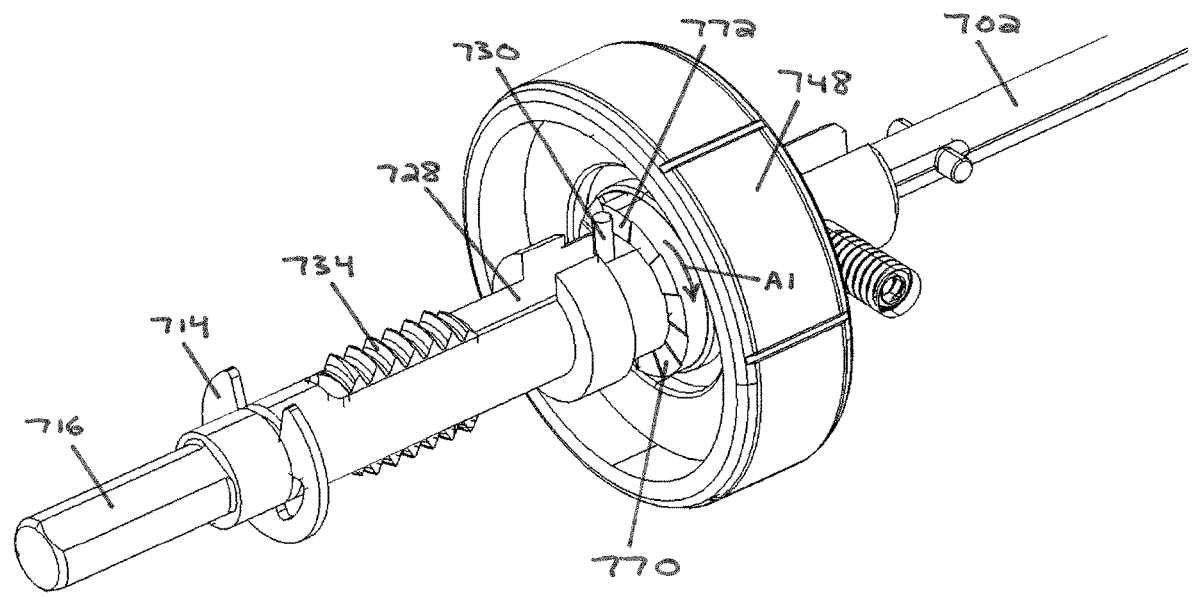
FIG. 7G is a perspective view of the proximal end of the cutting instrument of FIG. 7A shown with an actuation knob, bias spring, and forward handle portion removed.

As shown in FIGS. 7C-7D and 7G, a cylindrical proximal portion of the body 702 defines a first longitudinal slot 728 in which a first tab portion 730 of the actuation shaft 704 is slidably positioned. The slot 728 has a length that is greater than the length of the tab 730, such that the tab can slide longitudinally within the slot between a proximal position in which the blade 706 is fully-retracted and a distal position in which the blade is fully-deployed. The length of the slot 728 thus defines the range of diameters to which the blade 706 can be deployed and therefore the range of tunnel diameters that can be formed by the blade. As shown in FIG. 7G, the adjustment ring 748 includes a proximal-facing stepped stop surface 770. Accordingly, the length of the adjustment ring 748 differs at each of a plurality of discrete radial positions about the circumference of the stop surface 770. As shown in FIG. 7G, the adjustment ring 748 covers at least a distal portion of the slot 728, such that the distal travel limit of the tab 730 is defined by the stop surface 770. The effective length of the slot 728 can thus be changed by changing which step of the stop surface 770 is aligned with the slot. The illustrated stop surface 770 has a first step 772 at which the length of the adjustment ring 748 is at its maximum. The length of the adjustment ring 748 is reduced at each successive step as one moves in the direction of the arrow A1. Rotating the adjustment ring 748 in a first direction about the longitudinal axis L aligns taller steps of the stop surface 770 with the slot 728 to effectively reduce the length of the slot and thus decrease the maximum cutting diameter. Rotating the adjustment ring 748 in a second, opposite direction about the longitudinal axis L aligns shorter steps of the stop surface 770 with the slot 728 to effectively increase the length of the slot and thus increase the maximum cutting diameter.

The cylindrical proximal portion of the body 702 also defines upper and lower second longitudinal slots 732 in which upper and lower second tab portions 734 of the actuation shaft 704 are slidably positioned. The actuation knob 708 is coupled to the torque limiter 782, which is rotatably positioned over the cylindrical proximal portion of the body 702 such that a threaded interior surface of the torque limiter engages threaded surfaces of the upper and lower second tabs 734 of the actuation shaft 704.

The actuation knob 708 is sandwiched between a proximal retaining clip 714 and a shoulder 740 of the body 702. In operation, rotation of the actuation knob 708 relative to the body 702 and the forward handle portion 710 (which is pinned to the body to prevent rotation of the handle portion relative to the body) causes the threads of the actuation shaft 704 to ride along the threads of the torque limiter 782, thus causing the actuation shaft to translate longitudinally relative to the body. The distal limit of this longitudinal translation is defined by which step of the stop surface 770 is aligned with the first slot 728. The actuation knob 708 can be rotated in a first direction about the longitudinal axis L to pull the actuation shaft 704 proximally and retract the blade 706 and/or decrease the cutting diameter. The actuation knob 708 can also be rotated in a second, opposite direction about the longitudinal axis L to push the actuation shaft 704 distally and deploy the blade 706 and/or increase the cutting diameter.

As shown in FIGS. 7E-7F, the torque limiter 782 is received within a proximal cylindrical recess formed in the actuation knob 708 such that a series of teeth 784 formed on the distal-facing surface of the torque limiter engage a corresponding series of teeth 786 formed in the recess of the actuation knob. As the actuation knob 708 is rotated and the cutting blade 706 approaches or reaches the fully-deployed position, the first tab 730 on the actuation shaft 704 engages the stop surface 770, preventing further rotation of the torque limiter 782. If the user continues to apply torque to the actuation knob 708, the teeth 784, 786 temporarily disengage and the actuation knob 708 slips relative to the torque limiter 782. This slipping can generate tactile and/or audible feedback to the user indicating that the blade has reached the fully-deployed position. In addition, the slipping can prevent damage to the instrument 700 that might otherwise occur if excessive torque is applied after the blade reaches the fully-deployed position. The threshold torque at which the teeth 784, 786 disengage can be set to any desired value by varying the spring force of the bias spring 762 and/or the shape, ramp angle, or other properties of the teeth. In some embodiments, the instrument 700 can provide a similar torque limiting function as the blade 706 approaches or reaches the fully-retracted position.

As noted above, the position of the stop surface 770 can be adjusted by rotating the adjustment ring 748 relative to the body 702 and the forward handle 710. As shown in FIGS. 7D-7E, the handle 710 includes a plurality of protrusions 756 (four in the illustrated embodiment) that extend proximally from a proximal-facing end surface of the handle. The protrusions 756 can be received in any of a plurality of holes or detents 758 formed in the adjustment ring 748. Each of the holes 758 is indexed to a predetermined cutting diameter (e.g., such that movement of the protrusions 756 from one set of holes to an adjacent set of holes results in a 0.5 mm increase or decrease in cutting diameter depending on the direction of the adjacency). To adjust the diameter setting, the adjustment ring 748 is rotated to the desired setting (which can be indicated by markings on the adjustment ring and an indicator arrow 760 on the forward handle 710). As the adjustment ring 748 is rotated, the openings 758 formed therein cam over the dome-shaped protrusions 756, deflecting the adjustment ring 748 proximally against the resistance of the bias spring 762. When the protrusions 756 fall into an adjacent set of openings 758 in the adjustment ring 748, the adjustment ring springs distally under the force of the bias spring 762, providing tactile feedback to the user that the next setting has been reached.

In an exemplary method of using the instrument 700, the instrument can be prepared for use by a surgical technician on a "back table" before handing the instrument to the surgeon. This preparation can include setting the retro-cutting diameter using the adjustment ring 748 as described above and rotating the actuation handle 708 to position the blade 706 in the fully-retracted position. When the surgeon is ready to form a stepped opening, the surgeon actuates a drill to which the instrument 700 is coupled to form the reduced diameter portion of the opening with the forward cutting tip 718. The surgeon then rotates the actuation handle 708 until the actuation handle 708 slips relative to the torque limiter 782, which provides tactile and/or audible feedback to the surgeon to indicate that the blade 706 has been deployed to the pre-determined limit set by the surgical technician using the adjustment ring 748. The surgeon then actuates the drill to retro-cut the enlarged diameter portion of the stepped opening. Finally, the surgeon rotates the actuation handle 708 to return the cutting blade 706 to the fully-retracted position and withdraws the instrument 700 from the patient. Accordingly, the surgeon need not be concerned with setting the instrument 700 to the desired diameter while the instrument is in the patient. Rather, the desired diameter is pre-set and thus the surgeon can simply turn the actuation knob 708 until the stop surface 770 is engaged by the tab 730, reliably reaching the desired cutting diameter. In other words, the surgeon does not need to look at scales or calibrations when deploying the blade 706. The instrument 700 can also be used in other exemplary methods, as described further below.

The instruments disclosed herein can be constructed from any of a variety of known materials. Exemplary materials include those which are suitable for use in surgical applications, including metals such as stainless steel, polymers such as PEEK, ceramics, and so forth.

The instruments disclosed herein can be adjustable to any of a variety of diameters. In some embodiments, the instrument body has a diameter of about 3.5 mm with the blade completely retracted. In some embodiments, the blade can be deployed to a diameter in the range of about 3.5 mm to about 24 mm, in the range of about 3.5 mm to about 12 mm, in the range of about 6 mm to about 12 mm, in the range of about 6 mm to about 8 mm, in the range of about 8 mm to about 10 mm, or in the range of about 10 mm to about 12 mm. The instruments disclosed herein can be "analog" such that any diameter within a particular operating range can be selected by the user. The instruments disclosed herein can also be "digital" such that a finite plurality of discrete diameter settings are available to the user. These finite steps can be arranged in predetermined increments (e.g., quarter millimeter increments, half millimeter increments, one millimeter increments, and/or two millimeter increments).

As the above-described instruments are merely exemplary embodiments, it will be appreciated that the features of any particular instrument can be incorporated into any other instrument without departing from the scope of the present disclosure.

The opening through which the blade is deployed can be formed in any of a variety of locations along the length of the body. In some embodiments, the opening is formed just proximal to the distal tip of the body, for example, starting about 4 mm from the terminal distal end of the body and extending about 11 mm to a point that is about 15 mm from the terminal distal end of the body. The opening can also be formed at a greater distance from the distal tip of the body, for example at a midpoint of the body. As detailed below, this configuration can advantageously facilitate certain methods in which antegrade reaming of a femoral tunnel using an anteromedial approach is performed.

Methods

The instruments disclosed herein can be used in any of a variety of surgical methods, which can be performed on humans or animals. The instruments disclosed herein can also be used in non-surgical methods, for example in manufacturing or woodworking methods or in any other methods in which retrograde cutting, antegrade cutting, drilling, stepped tunnel formation, or other steps facilitated by said instruments are desired. It will be appreciated that the instruments disclosed herein can be used for both antegrade cutting and retrograde cutting.

In the methods described below, reference is made to the instrument 700 described above. It will be appreciated, however, that any of the other instruments disclosed or contemplated herein can be used to carry out these methods, with the methods being modified accordingly if necessary, as will be readily understood by those skilled in the art.

FIGS. 8A-8F illustrate an exemplary method of using a cutting instrument 700 to form a stepped bone tunnel in a femur 800. The method can employ a lateral approach as shown, or any other approach including a medial approach, an anterior approach, a posterior approach, an anteromedial approach, an anterolateral approach, a posteromedial approach, a posterolateral approach, etc. In addition, while a femur is used as an exemplary bone in which the tunnel is formed, it will be appreciated that the method can be used to form a tunnel in any bone or other object.

Figure 8A:
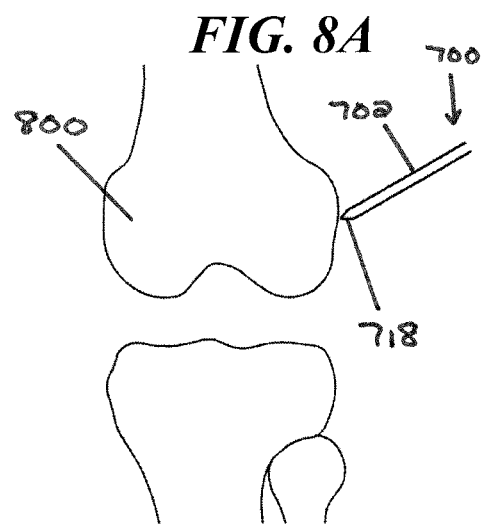
FIGS. 8A, 8B, 8C, 8D, 8E, and 8F illustrate an exemplary method of using a cutting instrument.
Figure 8B:
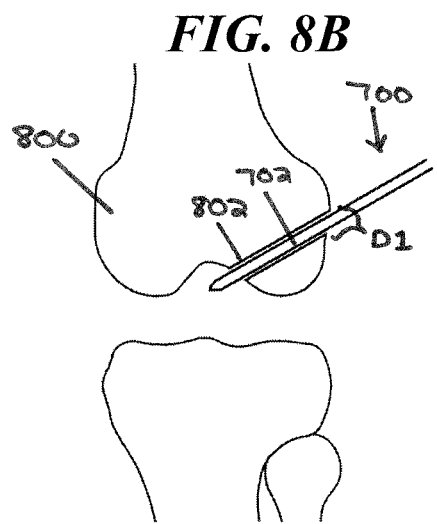
Figure 8C:
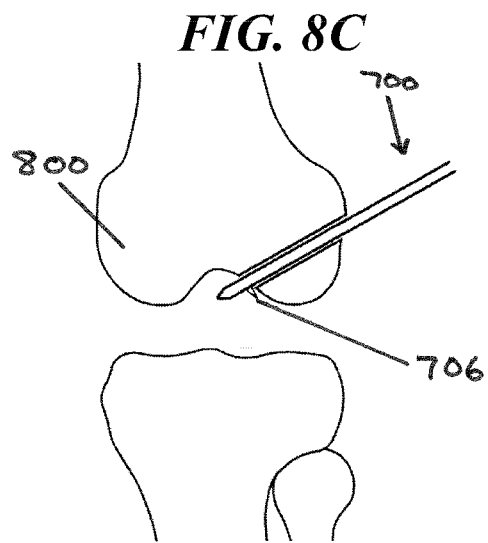
Figure 8D:
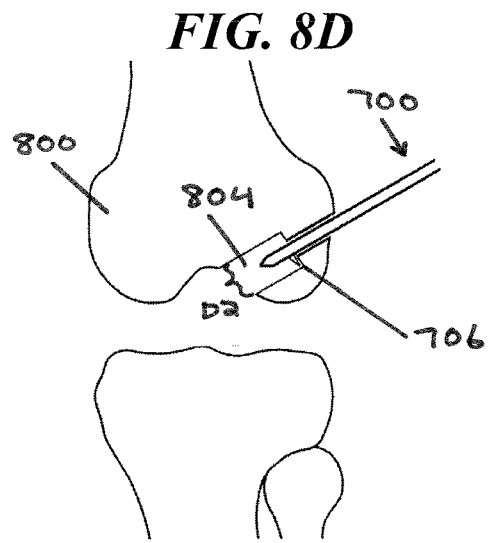
Figure 8E:
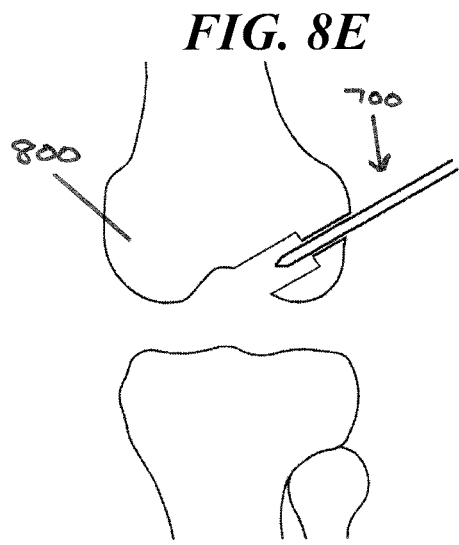
Figure 8F:
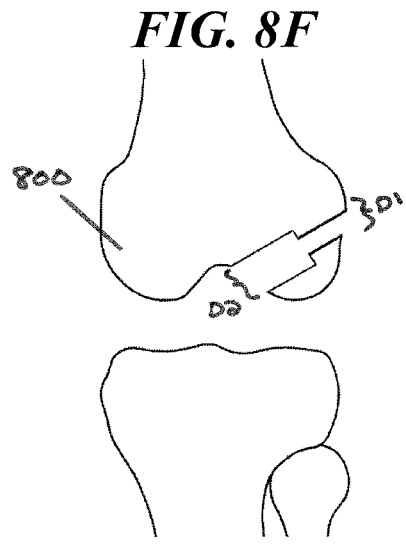

As shown in FIG. 8A, the distal drilling tip 718 of the instrument 700 can be targeted to a point on the exterior of the patient's femur 800 via an arthroscopic portal or an open skin incision. Prior to targeting the instrument 700 to the patient's femur 800, or at any other desired time, the actuation knob 708 of the instrument can be rotated in a first direction to fully-retract the cutting blade 706 and the adjustment ring 748 can be rotated to set the desired cutting diameter limit. These steps can be performed by a surgical technician on a back table of the operating room, before handing the instrument 700 to the surgeon. As shown in FIG. 8B, the surgeon can actuate a drill to which the cutting instrument 700 is coupled to form a first opening 802 in the femur 800 by antegrade cutting with the distal tip 718 of the cutting instrument. The first opening 802 has a diameter D1 which is substantially equal to the outside diameter of the body 702 of the cutting instrument 700. The first opening 802 can be formed to a desired depth, for example as indicated by depth markings and/or a depth stop on the exterior of the body 702 of the cutting instrument 700. As shown in FIG. 8C, with the distal end of the instrument 700 in the joint space, the surgeon can rotate the actuation knob 708 in a second, opposite direction until the cutting blade 706 has been deployed to the preset cutting diameter limit. As shown in FIG. 8D, the surgeon can then actuate the drill to form a second opening 804 in the femur 800 by retrograde cutting with the deployed cutting blade 706 of the instrument 700. The second opening 804 has a diameter D2 which is greater than the diameter D1 and which is substantially equal to the pre-set limit diameter. When the second opening 804 reaches the desired depth, which can be indicated to the surgeon by depth markings and/or a depth stop on the exterior of the body 702 of the cutting instrument 700, the actuation knob 708 can be rotated in the first direction to fully-retract the cutting blade 706 into the body, as shown in FIG. 8E. The cutting instrument 700 can then be withdrawn from the patient, as shown in FIG. 8F, leaving a stepped bone tunnel or socket in which a soft tissue graft can be mounted (e.g., to complete an ACL reconstruction or other procedure).

FIGS. 9A-9F illustrate an exemplary method of using a cutting instrument 700 to form a femoral socket using a trans-tibial approach. It will be appreciated that the method can use any of a variety of other approaches, and that the method can be used to form a socket in any other bone or object.

Figure 9A:
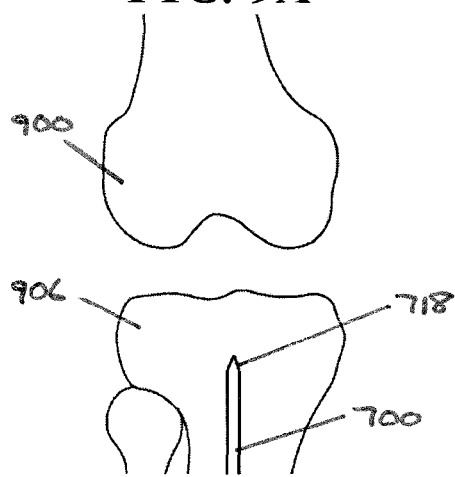
FIGS. 9A, 9B, 9C, 9D, 9E, and 9F illustrate another exemplary method of using a cutting instrument.
Figure 9B:
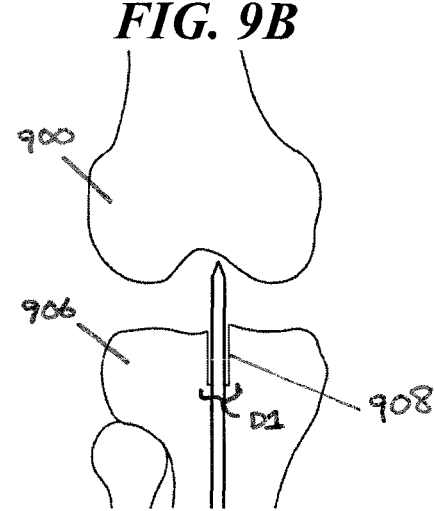
Figure 9C:
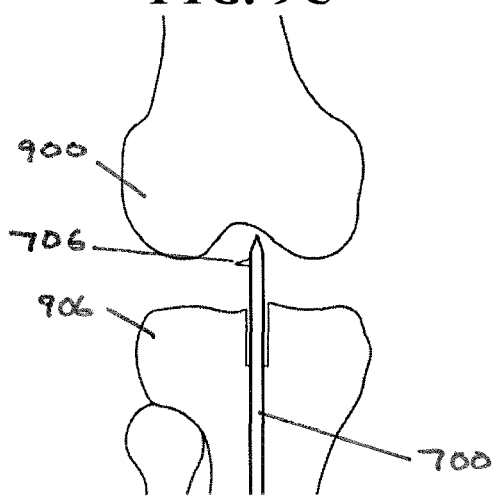
Figure 9D:
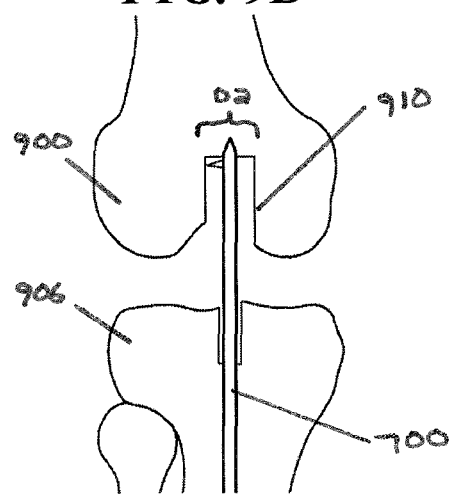
Figure 9E:
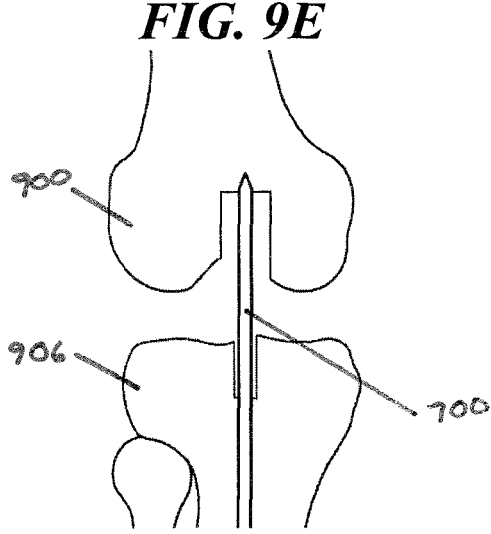
Figure 9F:
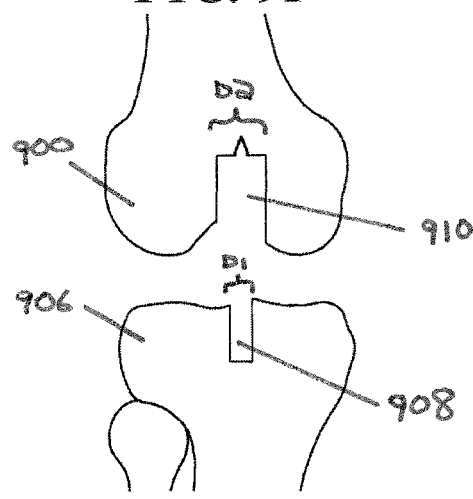

As shown in FIG. 9A, the distal drilling tip 718 of the instrument 700 can be targeted to a point on the exterior of the patient's tibia 906 via an arthroscopic portal or an open skin incision. Prior to targeting the instrument 700 to the patient's tibia 906, or at any other desired time, the actuation knob 708 of the instrument can be rotated in a first direction to fully-retract the cutting blade 706 and the adjustment ring 748 can be rotated to set the desired cutting diameter limit. These steps can be performed by a surgical technician on a back table of the operating room, before handing the instrument to the surgeon. As shown in FIG. 9B, the surgeon can actuate a drill to which the cutting instrument 700 is coupled to form a first opening 908 in the tibia 906 by antegrade cutting with the distal tip 718 of the cutting instrument. The first opening 908 has a diameter D1 which is substantially equal to the outside diameter of the body 702 of the cutting instrument 700. The first opening 908 can be formed to a desired depth, for example as indicated by depth markings and/or a depth stop on the exterior of the body 702 of the cutting instrument 700. As shown in FIG. 9C, with the distal end of the instrument 700 in the joint space, the surgeon can rotate the actuation knob 708 in a second, opposite direction until the cutting blade 706 has been deployed to the preset cutting diameter limit. As shown in FIG. 9D, the surgeon can then actuate the drill to form a second opening 910 in the femur 900 by antegrade cutting with the deployed cutting blade 706 of the instrument 700. The second opening 910 has a diameter D2 which is greater than the diameter D1 and which is substantially equal to the pre-set limit diameter. When the second opening 910 reaches the desired depth, which can be indicated to the surgeon by depth markings and/or a depth stop on the exterior of the body 702 of the cutting instrument 700, the actuation knob 708 can be rotated in the first direction to fully-retract the cutting blade 706 into the body, as shown in FIG. 9E. The cutting instrument 700 can then be withdrawn from the patient, as shown in FIG. 9F, leaving a femoral socket 910 in which a soft tissue graft can be mounted (e.g., to complete an ACL reconstruction or other procedure).

FIGS. 10A-10F illustrate another exemplary method of using a cutting instrument 700 to form a femoral socket using an anteromedial approach. It will be appreciated that the method can use any of a variety of approaches, and that the method can be used to form a socket in any other bone or object.

Figure 10A:
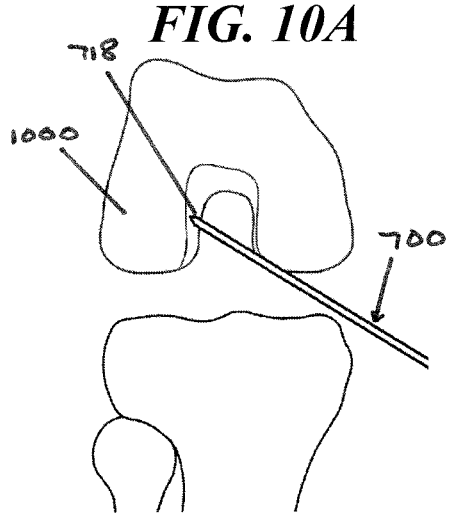
FIGS. 10A, 10B, 10C, 10D, 10E, and 10F illustrate another exemplary method of using a cutting instrument.
Figure 10B:
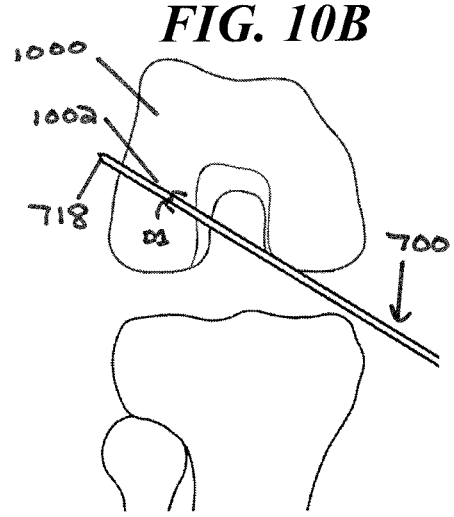
Figure 10C:
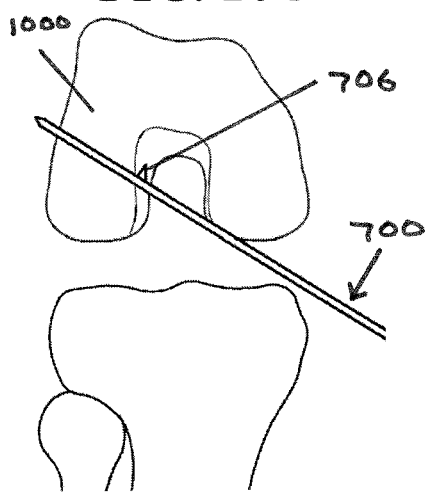
Figure 10D:
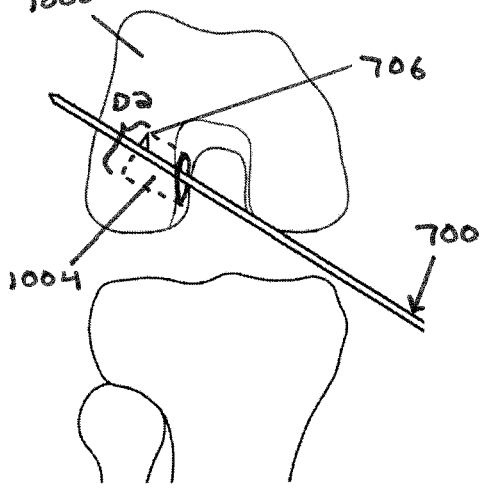
Figure 10E:
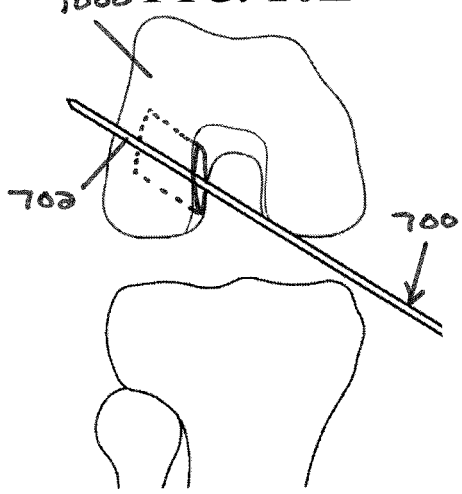
Figure 10F:
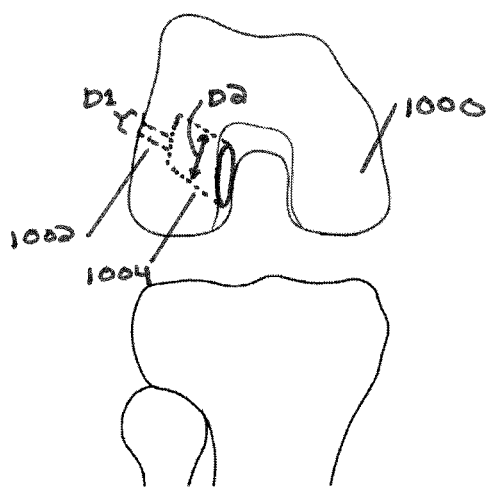

As shown in FIG. 10A, the distal drilling tip 718 of the instrument 700 can be targeted to a point within the femoral notch on the lateral condyle of the patient's femur 1000 via an arthroscopic portal or an open skin incision. In some embodiments, the instrument 700 can be at least partially inserted through an anteromedial portal, which can be formed, for example, about 1 cm medial to the patellar tendon and just distal to the inferior pole of the patella. Prior to targeting the instrument 700 to the patient's femur 1000, or at any other desired time, the actuation knob 708 of the instrument 700 can be rotated in a first direction to fully-retract the cutting blade 706 and the adjustment ring 748 can be rotated to set the desired cutting diameter limit. These steps can be performed by a surgical technician on a back table of the operating room, before handing the instrument 700 to the surgeon. As shown in FIG. 10B, the surgeon can actuate a drill to which the cutting instrument 700 is coupled to form a first opening 1002 through the lateral condyle of the femur by antegrade cutting with the distal tip 718 of the cutting instrument. There is little risk of damaging the cartilage on the medial condyle when forming the first opening 1002, as the outside diameter of the instrument 700 is relatively small as it passes the medial condyle. The first opening 1002 has a diameter D1 which is substantially equal to the outside diameter of the body 702 of the cutting instrument 700. The first opening 1002 can be formed to a desired depth, for example as indicated by depth markings and/or a depth stop on the exterior of the body 702 of the cutting instrument 700. As shown in FIG. 10C, with the midpoint or a substantially middle section of the instrument 700 in the joint space, the surgeon can rotate the actuation knob 708 in a second, opposite direction until the cutting blade 706 has been deployed to the preset cutting diameter limit. As shown in FIG. 10D, the surgeon can then actuate the drill to enlarge a portion of the first opening 1002 by forming a second opening 1004 by antegrade cutting with the deployed cutting blade 706 of the instrument 700. Again, there is little risk of damaging the cartilage on the medial condyle when forming the second opening 1004, as the outside diameter of the portion of the instrument 700 adjacent to the medial condyle is relatively small. The second opening 1004 has a diameter D2 which is greater than the diameter D1 and which is substantially equal to the pre-set limit diameter. When the second opening 1004 reaches the desired depth, which can be indicated to the surgeon by depth markings and/or a depth stop on the exterior of the body 702 of the cutting instrument 700, the actuation knob 708 can be rotated in the first direction to fully-retract the cutting blade 706 into the body, as shown in FIG. 10E. The cutting instrument 700 can then be withdrawn from the patient, as shown in FIG. 10F, leaving a femoral socket 1004 in which a soft tissue graft can be mounted (e.g., to complete an ACL reconstruction or other procedure).

It will be appreciated that the instruments disclosed herein can be used in any of a variety of other methods.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces, and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of a instrument can utilize a variety of techniques for disassembly, cleaning/replacement, and reassembly. Use of such techniques, and the resulting reconditioned instrument, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the instrument is sterilized. This can be done by any number of ways known to those skilled in the art including beta or gamma radiation, ethylene oxide, steam, and a liquid bath (e.g., cold soak).

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A cutting instrument, comprising:
an elongate body having a proximal end and a distal end defining an inner lumen therebetween, the elongate body having a longitudinal slot formed in an outer surface thereof;
a drilling tip at the distal end of the elongate body;
a cutting blade selectively disposed in the elongate body such that the cutting blade is positionable in a retracted position in which the cutting blade does not protrude from the elongate body and one or more deployed positions in which the cutting blade protrudes from the elongate body;
an actuation shaft that extends through the inner lumen, the actuation shaft having a tab that is configured to slide longitudinally within the longitudinal slot between a proximal position in which the cutting blade is fully-retracted and a distal position in which the blade is fully-deployed; and
an adjustment ring disposed around the elongate body such that the adjustment ring is configured to cover at least a portion of the longitudinal slot, a length of the longitudinal slot covered by the adjustment ring being adjustable such that the length defines a range of diameters to which the blade is configured to be deployed.

2. The instrument of claim 1, wherein the tab has a plurality of intermediate positions at which the blade protrudes from the elongate body such that an angle of the blade with respect to the body is smaller than an angle of the blade with respect to the body when the blade is fully deployed.

3. The instrument of claim 1, wherein the adjustment ring includes a stepped stop surface having a plurality of steps configured to engage the tab to limit distal travel of the tab within the longitudinal slot.

4. The instrument of claim 3, wherein different steps of the plurality of steps are configured to correlate with different lengths of the longitudinal slot.

5. The instrument of claim 3, wherein a length of the adjustment ring differs at each of a plurality of discrete radial positions about the circumference of the stepped stop surface.

6. The instrument of claim 3, wherein the adjustment ring is adjustable such that one or more steps of the plurality of steps are aligned with the slot to increase or decrease the length of the slot.

7. The instrument of claim 1, wherein translation of the actuation shaft relative to the elongate body along a longitudinal axis extending through the elongate body from the proximal end to the distal end causes the blade to move towards at least one of the fully-deployed position and the fully-retracted position.

8. The instrument of claim 1, further comprising:
a plurality of holes formed in the adjustment ring with each of the plurality of holes indicating a predetermined cutting diameter; and
a handle having a plurality of protrusions disposed thereon, the protrusions being configured to be received in the plurality of holes to set the predetermined cutting diameter.

9. The instrument of claim 8, further comprising a bias spring that is configured to urge the adjustment ring distally to provide tactile feedback to the user that the predetermined cutting diameter has been reached.

10. The instrument of claim 1, wherein the blade is deployed to a diameter in the range of about 6 mm to about 12 mm.

11. The instrument of claim 1, further comprising a cavity in which the cutting blade is pivotally mounted.

12. The instrument of claim 11, wherein the cavity is formed about 4 millimeters from a terminal end of the distal tip and extends to a point that is about 15 millimeters from a terminal end of the distal tip.

13. A surgical method for forming an opening in a surgical site, comprising:
setting a predetermined cutting diameter limit of a blade housed in a lumen of an elongate body of a cutting instrument to one of a plurality of full-deployed positions, the blade being configured to cut an opening at each of the fully-deployed positions;
operating the cutting instrument to form a first opening at a surgical site with a drilling tip of the cutting instrument while the blade is disposed within the elongate body, in an undeployed position;
deploying the blade to the predetermined cutting diameter limit; and
operating the cutting instrument to form a second opening in communication with the first opening with the blade.

14. The method of claim 13, wherein setting the predetermined cutting diameter limit further comprises moving an adjustment ring disposed around the elongate body relative to the elongate body to a position in which the adjustment ring covers at least a portion of a longitudinal slot formed in an outer surface of the elongate body, a length of the longitudinal slot covered by the adjustment ring defining a range of diameters to which the blade is configured to be deployed.

15. The method of claim 14, wherein moving the adjustment ring further comprises rotating the adjustment ring to align a step of a plurality of steps of a stop surface of the adjustment ring with the slot, the stop surface facing a distal end of the cutting instrument.

16. The method of claim 15, wherein rotating the adjustment ring reduces or increases the length of the adjustment ring depending on the step of the plurality of steps that is aligned with the slot.

17. The method of claim 15, wherein setting the predetermined cutting diameter limit further comprises rotating the adjustment ring between a first direction about a longitudinal axis of the elongate body to align taller steps of the plurality of steps with the slot to reduce the length of the slot and decrease a maximum cutting diameter of the blade and a second, opposite direction about the longitudinal axis of the elongate body to align shorter steps of the plurality of steps with the slot to increase the length of the slot and increase the maximum cutting diameter of the blade.

18. The method of claim 13, wherein deploying the blade to the predetermined cutting diameter limit further comprises rotating an actuation knob disposed around the elongate body between a first direction about a longitudinal axis of the elongate body to move an actuation shaft disposed within the lumen of the elongate body relative to the elongate body along the longitudinal axis and retract the blade to decrease the cutting diameter and a second, opposite direction about the longitudinal axis of the elongate body to move the actuation shaft relative to the elongate body along the longitudinal axis and deploy the blade to increase the cutting diameter.

19. The method of claim 18, wherein deploying the blade to the predetermined cutting diameter limiting further comprises rotating the actuation knob until a tab of the actuation shaft engages a stop surface of an adjustment ring disposed around the elongate body to prevent distal translation of the actuation shaft, the stop surface facing a distal end of the cutting instrument.

20. The method of claim 19, wherein further rotation of the actuation knob generates at least one of tactile feedback or audible feedback to indicate that the blade has reached the predetermined cutting diameter limit.

\* \* \* \* \*